(12) United States Patent
Li et al.

(10) Patent No.: US 10,046,178 B2
(45) Date of Patent: *Aug. 14, 2018

(54) AUTOMATIC CORRELATION MODELING OF AN INTERNAL TARGET

(71) Applicant: ACCURAY INCORPORATED, Sunnyvale, CA (US)

(72) Inventors: Shutian Li, Foster City, CA (US); Ye Sheng, San Jose, CA (US); Sohail Sayed, San Ramon, CA (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/991,428

(22) Filed: Jan. 8, 2016

(65) Prior Publication Data

US 2016/0121140 A1    May 5, 2016

Related U.S. Application Data

(63) Continuation of application No. 11/977,895, filed on Oct. 26, 2007, now Pat. No. 9,248,312.

(51) Int. Cl.
| | | |
|---|---|---|
| G06K 9/00 | (2006.01) | |
| A61N 5/10 | (2006.01) | |
| A61B 6/00 | (2006.01) | |
| A61B 5/11 | (2006.01) | |
| A61B 90/00 | (2016.01) | |

(Continued)

(52) U.S. Cl.
CPC ............ *A61N 5/1049* (2013.01); *A61B 5/113* (2013.01); *A61B 5/1127* (2013.01); *A61B 5/7246* (2013.01); *A61B 5/7292* (2013.01); *A61B 6/541* (2013.01); *A61N 5/103* (2013.01); *A61N 5/107* (2013.01); *A61N 5/1077* (2013.01); *A61B 5/1135* (2013.01); *A61B 5/7285* (2013.01); *A61B 2034/105* (2016.02); *A61B 2034/107* (2016.02); *A61B 2090/3945* (2016.02); *A61B 2090/3966* (2016.02); *A61B 2560/0475* (2013.01); *A61N 5/1037* (2013.01); *A61N 2005/1051* (2013.01); *A61N 2005/1061* (2013.01); *A61N 2005/1074* (2013.01)

(58) Field of Classification Search
None
See application file for complete search history.

(56) References Cited

U.S. PATENT DOCUMENTS

| | | | |
|---|---|---|---|
| 5,251,128 | A | 10/1993 | Crawford |
| 5,287,276 | A | 2/1994 | Crawford et al. |

(Continued)

FOREIGN PATENT DOCUMENTS

| | | |
|---|---|---|
| DE | 10310127 | 9/2004 |
| WO | 99/27839 | 6/1999 |

(Continued)

OTHER PUBLICATIONS

Office Action for Japanese Application No. 2010-530996, dated May 29, 2013, 11 pages.

(Continued)

*Primary Examiner* — Vikkram Bali
(74) *Attorney, Agent, or Firm* — Womble Bond Dickinson (US) LLP; Daniel Ovanezian

(57) ABSTRACT

A method and apparatus to automatically control the timing of an image acquisition by an imaging system in developing a correlation model of movement of a target within a patient.

11 Claims, 16 Drawing Sheets

(51) Int. Cl.
     *A61B 34/10*   (2016.01)
     *A61B 5/113*   (2006.01)
     *A61B 5/00*    (2006.01)

(56) References Cited

U.S. PATENT DOCUMENTS

| | | |
|---|---|---|
| 5,538,494 A | 7/1996 | Matsuda |
| 5,727,554 A | 3/1998 | Kalend et al. |
| 5,764,723 A | 6/1998 | Weinberger |
| 6,076,005 A | 6/2000 | Sontag et al. |
| 6,144,875 A | 11/2000 | Schweikard et al. |
| 6,307,914 B1 | 10/2001 | Kunieda et al. |
| 6,314,312 B1 | 11/2001 | Wessels et al. |
| 6,341,179 B1 | 1/2002 | Stoyle et al. |
| 6,385,286 B1 | 5/2002 | Fitchard |
| 6,468,265 B1 | 10/2002 | Evans et al. |
| 6,507,981 B1 | 1/2003 | Bosak, III et al. |
| 6,662,036 B2 | 12/2003 | Cosman |
| 6,690,965 B1 | 2/2004 | Riaziat et al. |
| 6,704,691 B2 | 3/2004 | Chiou |
| 6,731,970 B2 | 5/2004 | Schlossbauer |
| 6,778,850 B1 | 8/2004 | Adler |
| 6,804,548 B2 | 10/2004 | Takahashi et al. |
| 6,841,389 B2 | 1/2005 | Novikov et al. |
| 6,937,696 B1 | 8/2005 | Mostafavi |
| 6,973,202 B2 | 12/2005 | Mostafavi |
| 7,085,342 B2 | 8/2006 | Younis et al. |
| 7,171,257 B2 | 1/2007 | Thompson |
| 7,237,556 B2 | 7/2007 | Smothers et al. |
| 7,367,955 B2 | 5/2008 | Zhang et al. |
| 7,668,585 B2 | 2/2010 | Green |
| 7,822,176 B2 | 10/2010 | Yi et al. |
| 2001/0014772 A1 | 8/2001 | Lampotang |
| 2003/0033120 A1 | 2/2003 | Chiou |
| 2004/0071337 A1 | 4/2004 | Jeung |
| 2004/0092815 A1 | 5/2004 | Schweikard |
| 2004/0158146 A1 | 8/2004 | Mate |
| 2004/0254773 A1 | 12/2004 | Zhang et al. |
| 2005/0033154 A1 | 2/2005 | Decharms |
| 2005/0080332 A1 | 4/2005 | Shiu et al. |
| 2006/0074299 A1 | 4/2006 | Sayeh |
| 2006/0074304 A1 | 4/2006 | Sayed |
| 2007/0015991 A1 | 1/2007 | Fu et al. |
| 2007/0230765 A1 | 1/2007 | Wang et al. |
| 2007/0244386 A1 | 10/2007 | Steckner et al. |

FOREIGN PATENT DOCUMENTS

| | | |
|---|---|---|
| WO | 2002022686 | 3/2002 |
| WO | 03003796 | 1/2003 |
| WO | 2004044612 | 5/2004 |
| WO | 2005/030330 | 4/2005 |

OTHER PUBLICATIONS

Chinese Office Action for Chinese Application No. 200880113221.2, dated Apr. 3, 2013, 9 pages.

European Extended Search Report for European Patent Application No. 08841952.8, dated Dec. 3, 2010.

Accuray Treatment Delivery Manual, Jan. 2007.

Coste-Maniere, E., "Robotic whole body stereotactic radiosurgery: clinical advantages of the CyberKnifee integrated system", The International Journal of Medical Robotics +Computer Assisted Surgery, 2005, www.roboticpublications.com, 14 pages.

Mu, Zhiping, et al., "Multiple Fiducial Identification Using the Hidden Markov Model in Image Guided Radiosurgery," 0-7695-2646-2/06 © 2006 IEEE, 8 pages.

International Search Report and Written Opinion of the International Searching Authority, PCT/US08/10749 filed Sep. 15, 2008, dated Nov. 25, 2008.

Qin-Sheng Chen et al., "Fluoroscopic study of tumor motion due to breathing: Facilitating precise radiation therapy for lung cancer patients", Med. Phys. 28 (9), Sep. 2001, pp. 1850-1856.

Hiroki Shirato et al., "Intrafractional Tumor Motion: Lung and Liver", Seminars in Radiation Oncology, vol. 14, No. 1 Jan. 2004: pp. 10-18.

Data Points on Path of Movement

Data Points on Time Scale

AUTOMATIC CORRELATION MODELING OF AN INTERNAL TARGET

RELATED APPLICATION

This application is a continuation to U.S. patent application Ser. No. 11/977,895, filed Oct. 26, 2007, which are hereby incorporated by reference in its entirety.

TECHNICAL FIELD

This invention relates to the field of radiation treatment and, in particular, to tracking target movement in radiation treatment.

BACKGROUND

Pathological anatomies such as tumors and lesions can be treated with an invasive procedure, such as surgery, but can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of X-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted.

In many medical applications, it is useful to accurately track the motion of a moving target in the human anatomy. For example, in radiosurgery, it is useful to accurately locate and track the motion of a target, due to respiratory and other patient motions during the treatment. Conventional methods and systems have been developed for performing tracking of a target treatment (e.g. radiosurgical treatment) on an internal target, while measuring and/or compensating for breathing and/or other motions of the patient. For example, U.S. Pat. Nos. 6,144,875 and 6,501,981, commonly owned by the assignee of the present application, describe such conventional systems. The SYNCHRONY® system, developed by Accuray, Inc., Sunnyvale, Calif., can carry out the methods and systems described in the above applications.

These conventional methods and systems correlate internal organ movement with respiration in a correlation model. The correlation model includes mappings of outside movement of an external marker to the internal tumor locations obtained through X-ray imaging. In setting up the correlation model before treatment, these conventional methods and systems obtain X-ray images through a respiratory cycle of a patient. However, these conventional methods and systems rely on an operator to manually trigger the imaging system to acquire the image. It has been a challenge for operators to manually acquire evenly-distributed model points of the respiratory cycle for the correlation model. Manually triggering the images results in inconsistent distribution of model points of the respiratory cycle of the patient. Correlation models with evenly-distributed model points provide a more realistic model of the mappings of the outside movement of the external marker to the internal tumor locations. As such, using the conventional methods and systems, the quality of the initial correlation model, which depends on the ability of the operator to guess at when to manually trigger the imaging system to acquire the images, is not as good as the quality of a correlation model having evenly-distributed model points.

In one conventional method, the operator manually watches the external marker movement and the imaging history, such as on a display, to find an imaging timing pattern, and clicks a button to capture the next image based on the external marker movement and image history. The operator then waits for the result to see whether the image was acquired at the desired location of the respiratory cycle. In some instances to overcome the uneven distribution of model points, the operator acquires additional images to get a model point (e.g., image) at the desired location, resulting in an increase of unnecessary imaging occurrences. In addition, in the conventional methods and systems, there may be a significant delay between when the operator manually triggers the imaging system to acquire an image and when the imaging system actually acquires the image. This delay complicates the manual timing process to determine when, in the respiratory cycle, the operator should manually trigger the imaging system to acquire an image at the desired location of the respiratory cycle.

BRIEF DESCRIPTION OF THE DRAWINGS

The present invention is illustrated by way of example, and not by way of limitation, in the figures of the accompanying drawings.

DETAILED DESCRIPTION

Figure 1:
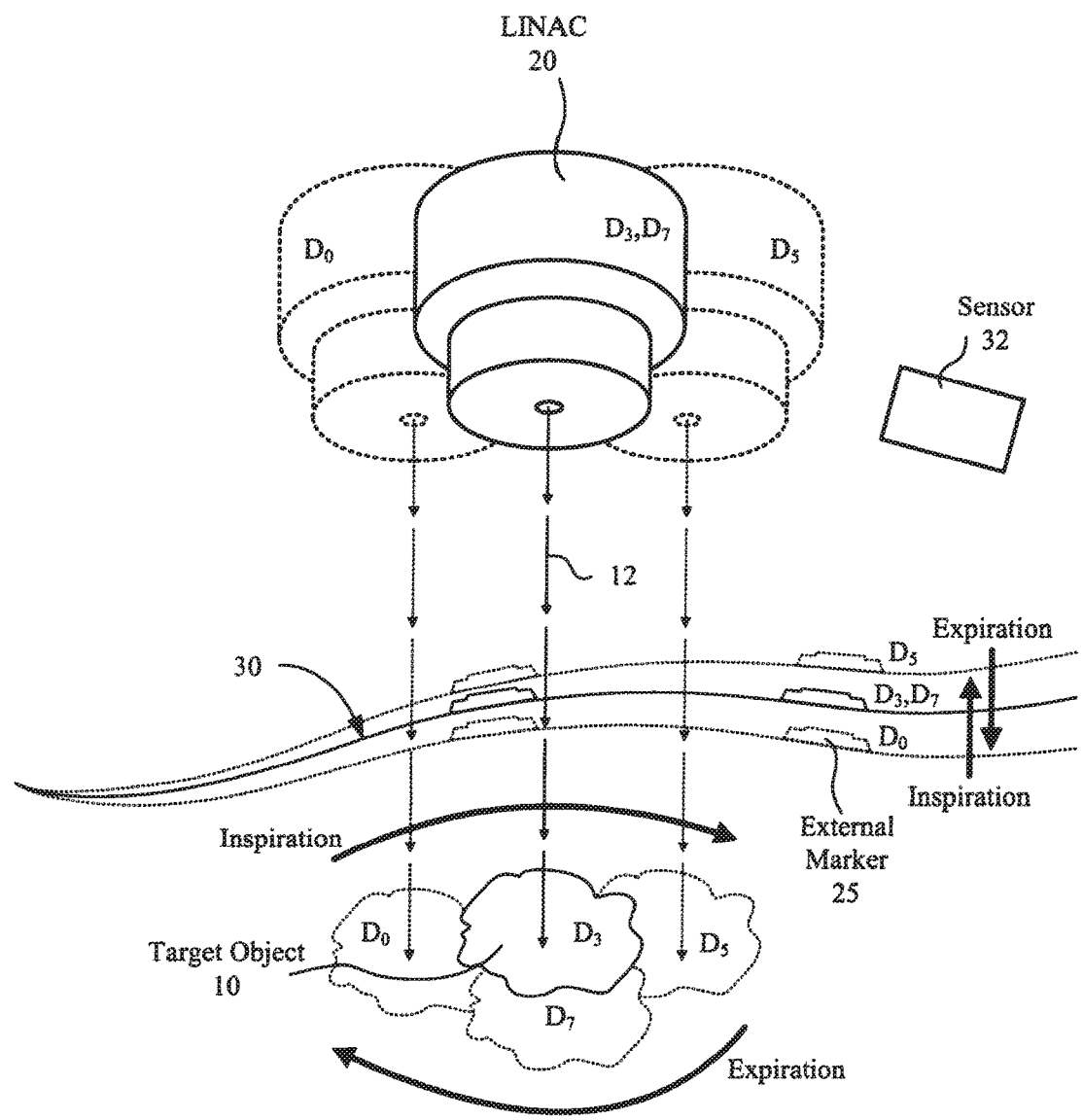
FIG. 1 illustrates a cross-sectional view of a treatment tracking environment.

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of the present invention include various operations, which will be described below. These operations may be performed by hardware components, software, firmware, or a combination thereof.

Certain embodiments may be implemented as a computer program product which may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage media (e.g., floppy diskette); optical storage media (e.g., CD-ROM); magneto-optical storage media; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of media suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Embodiments of a method and system to automatically trigger imaging at desired times in a periodic cycle of a patient, for example, the respiratory cycle, heartbeat cycle, or the like. As described above, a target within a patient may move due to respiratory motion, cardiac motions, or other patient motions. These patient motions may be periodic in nature. The periodic cycle of these motions can be measured by external sensors, such as a tracking sensor that tracks internal or external markers associated with a patient, a heart beat monitor, or the like. Historical data of previous periodic cycles, as measured by the external sensors, can be used to predict when to automatically acquire images in one or more subsequent cycles in order to develop an evenly-distributed set of images for developing a correlation model. The correlation model may be used to track the movement of the internal target during treatment.

As described above, using manual triggering, the result of X-ray imaging happens in a random fashion, namely, the user clicks the acquire button randomly and there is a random system delay between when the user clicks the acquire button and when the images are taken. Using the automatic triggering embodiments described herein, the result of the X-ray imaging is controlled by current LED signals (e.g., representative of the movement of the external markers), and when the LED moves into a desired triggering location, the triggering event happens and the images are at the desired triggering location. The embodiments described herein provide a new communication channel to automatically trigger imaging in real time at the specified times of the periodic cycle. The embodiments described herein also provide a new algorithm to calculate the desired times in the respiratory cycle for automatic modeling. The embodiments described herein may also provide a user interface to help a user achieve automatic modeling with substantially evenly-distributed images (e.g., model points) of the target during the respiratory cycle. The embodiments described herein are directed at providing a mechanism with minimal user interaction to achieve automatic modeling of the movement of the target for tracking the movement of the target. The embodiments described herein may be implemented in already existing target locating systems with minimal impact to the preexisting architecture, or alternatively, in newly developed target locating systems.

As described above, a correlation model is developed to correlate internal organ movement with respiration. The correlation model includes mappings of one or more external markers to the internal target position (e.g., tumor location) obtained through real-time X-ray imaging. The embodiments described herein, however, do not create the correlation model manually, by manually triggering the acquisition of each X-ray image to add a model point, and do not manually control the timing of X-ray image acquisition to acquire a model point at a desired location in the breathing waveform, which represents the periodic cycle of the next model point. Instead in some embodiments, the correlation model is created automatically, by automatically triggering the acquisition of each X-ray image to add a model point, by automatically controlling the timing of the X-ray image acquisition to acquire the model point at a desired location in the breathing waveform, which represents the periodic cycle of the next model point. In one embodiment, the method and system control both the timing of the next X-ray image and the location of the model point in a breathing waveform (e.g., phase in respiratory cycle). In another embodiment, an operator specifies the desired location of a model point in the breathing waveform (e.g., phase in respiratory cycle), and the method and system control the timing of the next X-ray image to acquire a model point in that desired location. Although some of the embodiments described below are directed to controlling the timing of automatically acquiring images for model points in the breathing waveform (e.g., respiratory cycle), in other embodiments, the automatic image acquisition can be performed for other types of waveforms, such as heartbeat cycles of a patient, or other waveforms of other periodic motions of the patient.

In one embodiment, the method and system are described to automatically acquire pretreatment images of an internal target of a patient before treatment and to generate a correlation model that maps movement of an external marker to a target location of a target using the pretreatment images. In one embodiment, a method and system are presented to identify the correlation between movement(s) of a target, such as an internal organ, and respiration (or other motion such as heartbeat) of a patient. These movements may include linear movements, non-linear movements, and asymmetric movements. In one embodiment, the method and system may facilitate modeling movement paths of a target that moves along different paths during inspiration and expiration, respectively. One embodiment of automatically triggering the pretreatment images includes automatically determining the periodic cycle of the patient, automatically determining specified times in the periodic cycle at which to acquire the pretreatment images, and automatically sending commands to an imaging system to acquire the pretreatment images at the specified times.

In one embodiment, generating the correlation model includes acquiring data points representative of positions over time of an external marker associated with the patient. In one embodiment, the external marker defines an external path of movement of the external marker during the respiratory cycle of the patient. The data points correspond to the pretreatment images. The method and system identifies a path of movement of the target based on the data points and the pretreatment images, and develops the correlation model using the path of movement of the target.

The method and system may consider position, speed, and/or direction of respiration or the internal object to develop one or more correlation models. The method and system also may use data points in time for which the position of the target is known. Respiration may be monitored in parallel with the monitoring of the target position. Information about the position and the speed/direction of respiration may be obtained at the time of interest. Once established, a correlation model may be used along with a respiration monitoring system to locate and track the internal movement of a target, such as an organ, region, lesion, tumor, and so forth.

FIG. 1 illustrates a cross-sectional view of a treatment tracking environment. The treatment tracking environment depicts corresponding movements of an internal target 10 within a patient, a linear accelerator (LINAC) 20, and an external marker 25. The illustrated treatment tracking environment is representative of a patient chest region, for example, or another region of a patient in which an internal organ might move during the respiratory cycle of the patient. In general, the respiratory cycle of a patient will be described in terms of an inspiration interval and an expiration interval, although other designations and/or delineations may be used to describe a respiratory cycle.

In one embodiment, the LINAC 20 moves in one or more dimensions to position and orient itself to deliver a radiation beam 12 to the target 10. Although substantially parallel radiation beams 12 are depicted, the LINAC 20 may move around the patient in multiple dimensions to project radiation beams 12 from several different locations and angles. The LINAC 20 tracks the movement of the target 10 as the patient breathes, for example. One or more external markers 25 are secured to, or otherwise disposed on, the exterior 30 of the patient in order to monitor the patient's breathing cycle. In one embodiment, the external marker 25 may be a device such as a light source (e.g., light emitting diode (LED)) or a metal button attached to a vest worn by the patient. Alternatively, the external marker 25 may be attached to the patient's clothes or skin in another manner.

As the patient breathes, a tracking sensor 32 tracks the location of the external marker 25. For example, the tracking sensor may track upward movement of the external marker 25 during the inspiration interval and downward movement of the external marker 25 during the expiration interval. The relative position of the external marker 25 is correlated with the location of the target 10, as described below, so that the LINAC 20 may move relative to the location of the external marker 25 and the correlated location of the target 10. In another embodiment, other types of external or internal markers may be used instead of, or in addition to, the illustrated external marker 25.

As one example, the depicted target 10 is shown in four positions, designated as $D_0$, $D_3$, $D_5$, and $D_7$. The first position, $D_0$, may correspond to approximately the beginning of the inspiration interval. The second position, $D_3$, may correspond to a time during the inspiration interval. The third position, $D_5$, may correspond to approximately the end of the inspiration interval and the beginning of the expiration interval. The fourth position, $D_7$, may correspond to a time during the expiration interval. Additional positions of the target 10 on the path of movement are graphically shown and described in more detail with reference to the following figures. As the patient breathes, the target 10 may move along a path within the patient's body. In one embodiment, the path of the target 10 is asymmetric in that the target 10 travels along different paths during the inspiration and expiration intervals. In another embodiment, the path of the target 10 is at least partially non-linear. The path of the target 10 may be influenced by the size and shape of the target 10, organs and tissues surrounding the target 10, the depth or shallowness of the patient's breathing, and so forth.

Similarly, the external marker 25 is shown in a first position, $D_0$, a second position, $D_3$, a third position, $D_5$, and a fourth position, $D_7$, which correspond to the positions of the target 10. By correlating the positions of the external marker 25 to the target 10, the position of the target 10 may be derived from the position of the external marker 25 even though the external marker 25 may travel in a direction or along a path that is substantially different from the path and direction of the target 10. The LINAC 20 is also shown in a first position, $D_0$, a second position, $D_3$, a third position, $D_5$, and a fourth position, $D_7$, which also correspond to the positions of the target 10. In this way, the movements of the LINAC 20 may be substantially synchronized to the movements of the target 10 as the position of the target 10 is correlated to the sensed position of the external marker 25.

Figure 2:
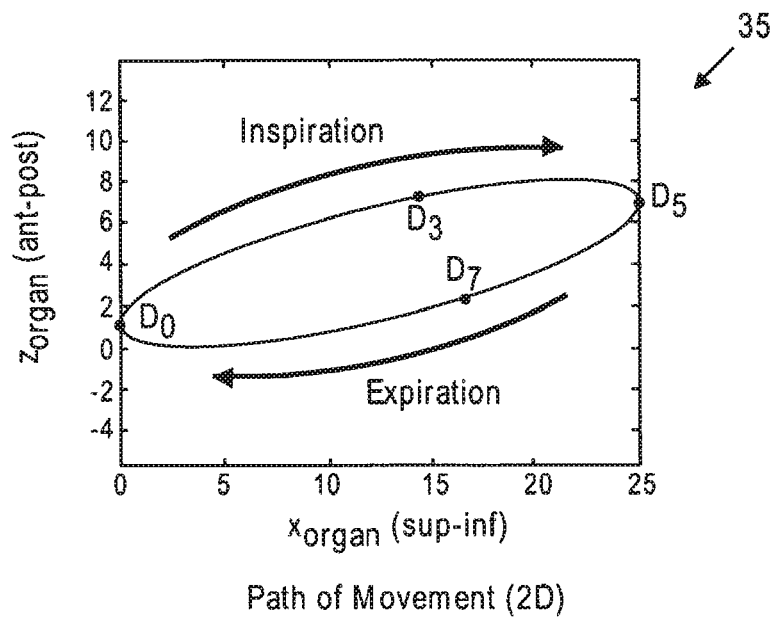
FIG. 2 is a graphical representation of an exemplary two-dimensional path of movement of an internal target during a respiration period.

FIG. 2 is a graphical representation 35 of an exemplary two-dimensional path of movement of an internal target 10 during a respiration period. The horizontal axis represents displacement (e.g., in millimeters) of the target 10 in a first dimension (x). The vertical axis represents displacement (e.g., in millimeters) of the target 10 in a second dimension (z). The target 10 may similarly move in a third dimension (y). As shown in the graph 35, the path of movement of the target 10 is non-linear. Additionally, the path of movement is different during an inspiration period and an expiration period. As an example, the inspiration path may correspond to the upper portion of the graph 35 between zero and twenty-five in the x direction, with zero being a starting reference position, $D_0$, and twenty-five being the maximum displacement position, $D_5$, at the moment between inspiration and expiration. The corresponding expiration period may be the lower portion of the graph 35 between $D_5$ and $D_0$. In the depicted embodiment, the displacement position $D_3$ is on the inspiration path roughly between $D_0$ and $D_5$. Similarly, the displacement position $D_7$ is on the expiration path roughly between $D_5$ and $D_0$. These displacement points are shown with additional displacement points in FIG. 4.

Figure 3:
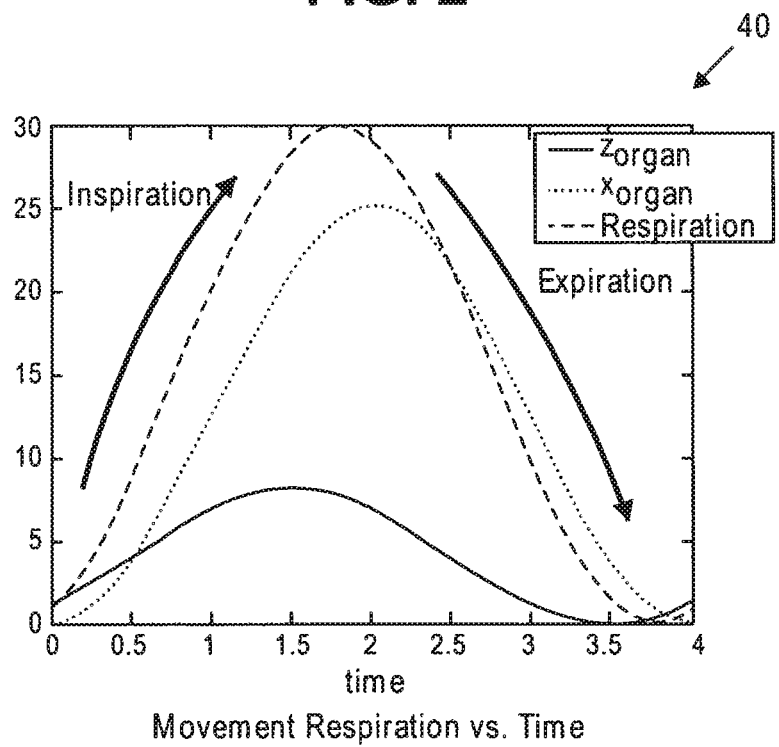
FIG. 3 is a graphical representation of an exemplary path of movement of an internal target during a respiration period, as a function of time.

FIG. 3 is a graphical representation 40 of an exemplary path of movement of an internal target 10 during a respiration period, as a function of time. The graph 40 shows the displacement (e.g., in millimeters) of the target 10 over time (e.g., in seconds) in the x direction (dashed line) and in the z direction (solid line). The graph 40 also shows the displacement (in millimeters) of, for example, an external marker 10 to identify the respiration period (dashed line). In the depicted embodiment, the external marker 25 is maximally displaced (approximately 30 mm) more than the target 10 in the x direction (approximately 25 mm) or in the z direction (approximately 8 mm). However, the maximum displacement of the target 10 in the various directions does not necessarily align with the maximum displacement of the external marker 25 associated with the respiratory cycle. Additionally, the maximum displacement of the target 10 in the one direction does not necessarily align with the maximum displacement in another direction. For example, the maximum displacement of the external marker 25 occur at approximately 1.75 s, while the maximum displacement of the internal organ 10 in the x and z directions may occur at approximately 2.0 and 1.5 seconds, respectively. These misalignments may be present in both the inspiration and expiration paths.

Figure 4:
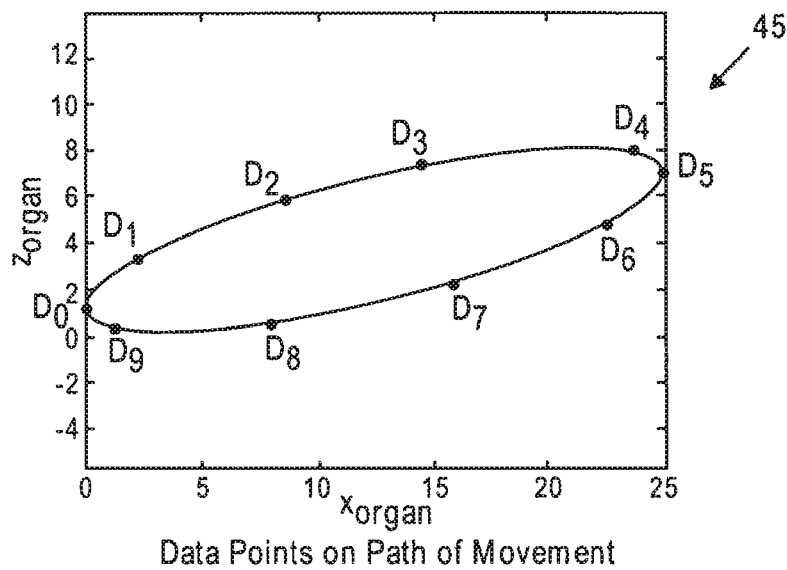
FIG. 4 is a graphical representation of an exemplary set of data points associated with the path of movement shown in FIG. 2.

FIG. 4 is a graphical representation 45 of an exemplary set of data points $D_0$-$D_9$ associated with the path of movement shown in FIG. 2. In particular, the data points $D_0$-$D_9$ are superimposed on the path of movement of the target 10. The data points $D_0$-$D_9$ correspond to various points in time during the respiration period. In the illustrated embodiment, one data point data point $D_0$ designates the initial reference location of the target 10 prior to the inspiration interval. Four data points $D_1$-$D_4$ designate the movement of the target 10 during the inspiration interval. The data point $D_5$ designates the moment between the inspiration and expiration intervals. The data points $D_6$-$D_9$ designate the movement of the target 10 during the expiration interval. The following table provides approximate coordinates for each of the data points $D_0$-$D_9$. Similar coordinates may be provided for the displacement of the external marker 25 or the displacement of the target 10 in another direction.

TABLE 1

Data Point Coordinates.

| Data Point | (x, z) (mm) |
| --- | --- |
| $D_0$ | (0, 1) |
| $D_1$ | (2, 3) |
| $D_2$ | (8, 5) |
| $D_3$ | (14, 7) |
| $D_4$ | (24, 8) |
| $D_5$ | (25, 7) |
| $D_6$ | (23, 5) |
| $D_7$ | (16, 2) |
| $D_8$ | (8, 0) |
| $D_9$ | (1, 0) |

Figure 5:
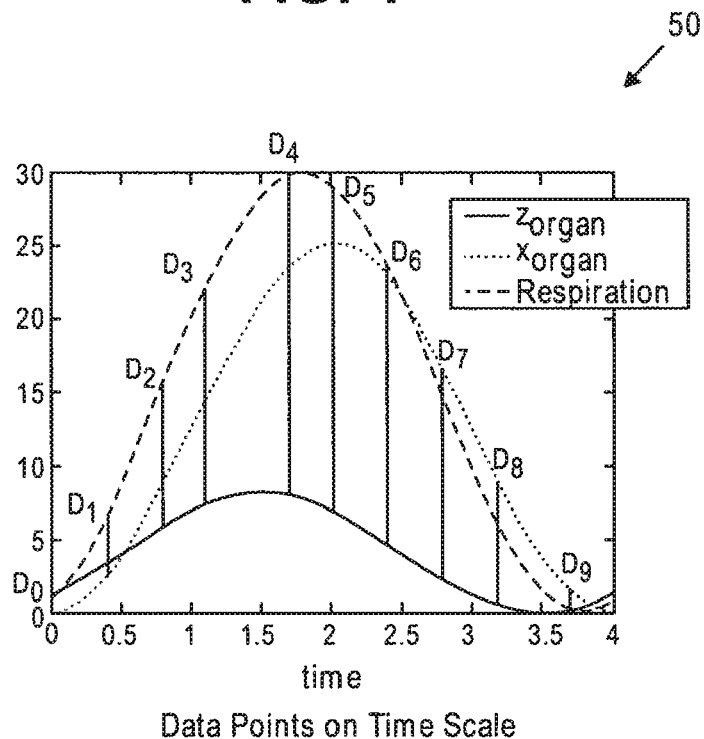
FIG. 5 is a graphical representation of an exemplary set of data points associated with the path of movement shown in FIG. 3.

FIG. 5 is a graphical representation 50 of the exemplary set of data points $D_0$-$D_9$ associated with the paths of movement shown in FIG. 3. The data points $D_0$-$D_9$ are represented by vertical lines superimposed on the path of movement of the target 10 and the external marker 25. The following table provides approximate times corresponding to each of the data points $D_0$-$D_9$, as well as approximate displacement values, r, for the external marker 25.

TABLE 2

Data Point Times.

| Data Point | Time (s) | r (mm) |
| --- | --- | --- |
| $D_0$ | 0.0 | 1 |
| $D_1$ | 0.4 | 6 |
| $D_2$ | 0.8 | 16 |
| $D_3$ | 1.1 | 22 |
| $D_4$ | 17 | 30 |
| $D_5$ | 2.4 | 28 |
| $D_6$ | 2.8 | 23 |
| $D_7$ | 3.2 | 14 |
| $D_8$ | 3.7 | 5 |
| $D_9$ | 4.0 | 0 |

Figure 6:
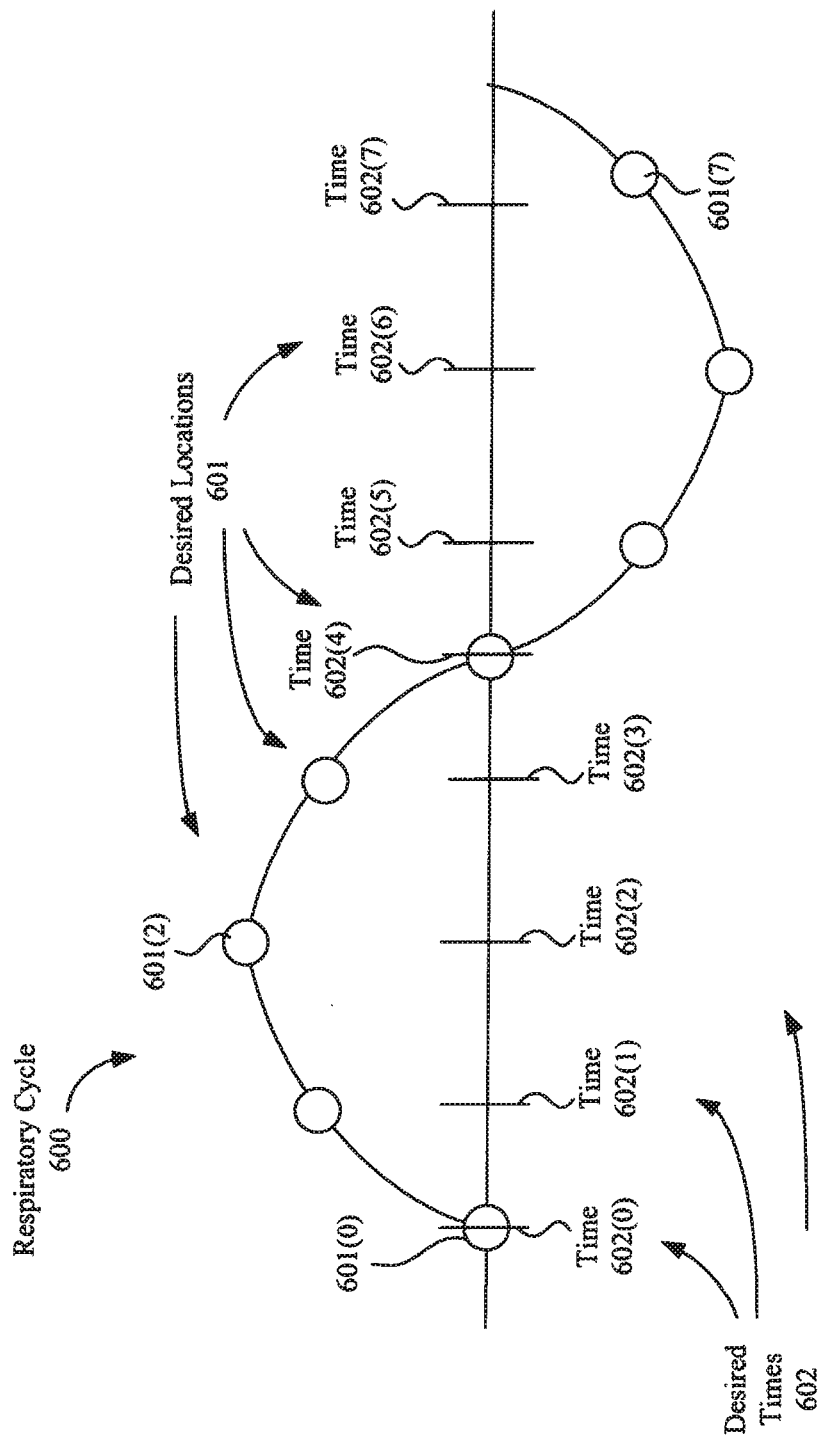
FIG. 6 illustrates one embodiment of an exemplary waveform representative of a respiratory cycle including multiple model points at multiple locations that each represents a phase of the respiratory cycle.

FIG. 6 illustrates one embodiment of an exemplary waveform representative of a respiratory cycle including multiple model points at multiple locations that each represents a phase of the respiratory cycle. The respiratory cycle waveform includes eight model points at desired locations 601. Each of the eight model points represent a different phase of the respiratory cycle 600. The model points above the line represent either inspiration or expiration, and the model points below the line represent the opposite of the model points above the line. It should be noted that the distance between the maximum and minimum model points represents the amplitude of the respiratory cycle. In one embodiment, the desired locations 601 are selected by an operator, and the system automatically triggers the acquisition of images at the desired times 602 to obtain an image for each of the model points at the desired locations 601. For example, the operator may specify the four desired locations 601(0), 601(2), 601(4), and 601(6), and in response the system determines to acquire images at times 602(0), 602(2), 602(4), and 6012(6) for the model points at the desired locations 601(0), 601(2), 601(4), and 601(6). In another embodiment, the desired locations 601 are automatically selected by the system, and the system automatically triggers the acquisition of images at the desired times. In these embodiments, the system attempts to achieve an optimal distribution of model points in the respiratory cycle 600 by automatically triggers the acquisition of images at the desired times.

It should be noted that eight model points are illustrated and described with respect to FIG. 6, however, in other embodiments, more or less than eight model points may be used, for example, in one embodiment, three model points may be used to create the correlation model.

The model points represent the different phases in the respiratory cycle 600 where X-ray image are to be acquired at the specified times. It should be noted that images for each of the model points are not necessarily acquired in the same respiratory cycle, but the model points of respiratory cycle 600 represents the different phases at the desired locations of the respiratory cycle at which images should be acquired. Similarly, the specified times 602 represent times in the respiratory cycle at which the image should be acquired, which may be in one or more different respiratory cycles. For example, the first model point at desired location 601(0) may be acquired during a first respiratory cycle at time 602(0), and a second model point at desired location 601(1) may be acquired during a second respiratory cycle at time 602(1).

In one embodiment, the operator clicks on a button, such as an "Acquire" button in a user interface, and the system automatically controls the timing of the X-ray image acquisition to add model points at the desired locations. The model points are automatically selected by the system. In another embodiment, the operator selects a desired location on the respiratory cycle 600 by clicking a model point, and clicks on the button (e.g., "Acquire" button) in the user interface, and the system automatically controls the timing of the X-ray image acquisition to add a model point at the user-selected desired location. In another embodiment, the user interface provides visual feedback of where in the respiratory cycle the image was acquired.

In one embodiment, the respiratory cycle 600 is determined using multiple data points of a position of an external marker associated with the patient over time, such as described with respect to the tracking sensor 32 and external marker 25 of FIG. 1. The positions of the external marker define an external path of movement of the external marker, which may be used to define the respiratory cycle. The model points at the desired locations 601 correspond to the data points on the waveform. A motion tracking system, including the tracking sensor 32, tracks the movement of one or more external markers and determines the position of the one or more external markers 25. The movement of the one or more external markers may be used to define the respiratory cycle 600 of the patient. The respiratory cycle 600 can then be used to determine the desired locations (e.g., different phases of the respiratory cycle) at which images should be acquired to generate the correlation model with substantially evenly-distributed model points. Using the data points and the images (e.g., model points) at the desired locations, a path of movement of the target within the patient is identified, and a correlation model is developed based on the path of movement of the target. To develop the correlation model, various types of curve fitting approximations may be used. In one embodiment, the correlation model is developed using a polynomial approximation of the path of movement of the target, such as described in application Ser. Nos. 11/239,789 and 11/240,593, both filed Sep. 29, 2005, which are commonly owned by the assignee of the present application. In one embodiment, the polynomial approximation is a second order polynomial. Alternatively, other types of approximations may be used to develop the correlation model.

In one embodiment, the correlation model is a linear correlation model. In this embodiment, two model points are used to determine the origin and the principal axis for the linear correlation model. Motion of the target that is linear uses this model type. In another embodiment, the correlation model is a curvilinear correlation model. The curvilinear correlation model is used when the target moves back and forth along an arc, that is, with curve motion. Typically, four model points or more are used to establish this type of model. In another embodiment, the correlation model is a dual-curvilinear correlation model. The dual-curvilinear correlation model is used when the target moves along an arc an uses different paths during inspiration and expiration, for example, due to respiration. Motion of the target is represented by two curvilinear paths to distinguish the model points that occurred during inspiration and expiration. Typically, seven model points or more are used to establish this type of model. Alternatively, the correlation model may be other types of models known to those of ordinary skill in the art. It should also be noted that the type of model may vary between each of the external markers.

In one embodiment, the waveform of the respiratory cycle 600 represents motion of one or more external markers (e.g., marker LEDs) due to respiration. Peaks and valleys in the waveform represent the two ends of the respiratory cycle of the patient, such as the start inspiration/expiration and end inspiration/expiration. Depending on the motion of each of the one or more external markers, peaks may correspond to full inspiration in one waveform and full expiration in another waveform. Each X-ray image acquired by a treatment delivery system (including an imaging system) adds a model point to the correlation model. In order to create an accurate and robust model, the model points should be distributed evenly and cover the whole range of respiratory motion. To distribute the model points evenly, the timing of the X-ray image acquisition is automatically controlled with the breathing motion, monitored by the one or more external markers. In one embodiment, three images are acquired to develop a correlation model; in particular, two images are used to build the correlation model, and one image is used to confirm the developed correlation model. In another embodiment, fifteen images are acquired and stored in the model data set at a time to develop the correlation model. Alternatively, other numbers of images may be used to develop the correlation model. In one embodiment, as additional images are acquired, the model data set is updated, and the updated model data set may be used to update the correlation model. In one embodiment, a first-in-first-out (FIFO) approach is used to update the data set. Alternatively, other types of approaches may be used to develop and update the correlation model.

In one embodiment, as illustrated in FIG. 6, eight images are acquired at eight different locations 601 at eight specified times 602. Acquiring eight images may be performed to ensure accuracy of the correlation model, despite various conditions, such as the target motion exceeding 20 millimeters (mm), the target motion suspected as being complex in nature, the target motion is out of phase with breathing motion, or the like. FIG. 6 illustrates when the X-ray images are substantially evenly distributed throughout the respiratory cycle 600. For example, the model points (e.g., X-ray images) at desired locations 601(2) and 602(6) are model points acquired at full inspiration and expiration, and the model points at desired locations 601(0) and 601(4) are model points acquired at midpoints of inspiration and expiration. The remaining model points at desired locations 601(1), 601(3), 601(5), and 601(7) are model points acquired at amplitudes halfway between the full and midpoint model points of the respiratory cycle 600. The model points at desired locations 601(0)-601(7) are substantially evenly distributed over the respiratory cycle 600.

Figure 7A:
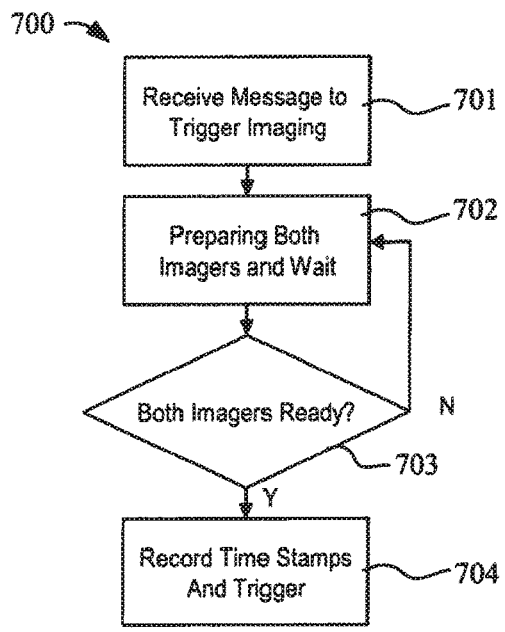
FIG. 7A illustrate a flow chart of manually triggering acquisition of an image by manually controlling the timing of the image acquisition.

FIG. 7A illustrate a flow chart of manually triggering acquisition of an image by manually controlling the timing of the image acquisition. Method 700 includes various operations to manually control the timing of acquiring an image for a desired location of the respiratory cycle. The imaging system receives from the target location system (TLS) a message to trigger imaging, operation 701. The message may be sent to the imaging system in response to an operation on the user interface, such as an operator clicking a button of the user interface to acquire an image. The imaging system prepares both imagers and waits, operation 702. The method 700 then determines if both imagers are ready, operation 703. If both imagers are not ready, the method 700 returns to operation 702. When both imagers are ready, the imaging system records the time stamps and triggers the imagers to acquire the image, operation 704. The time stamps may be sent back to the TLS.

Figure 7B:
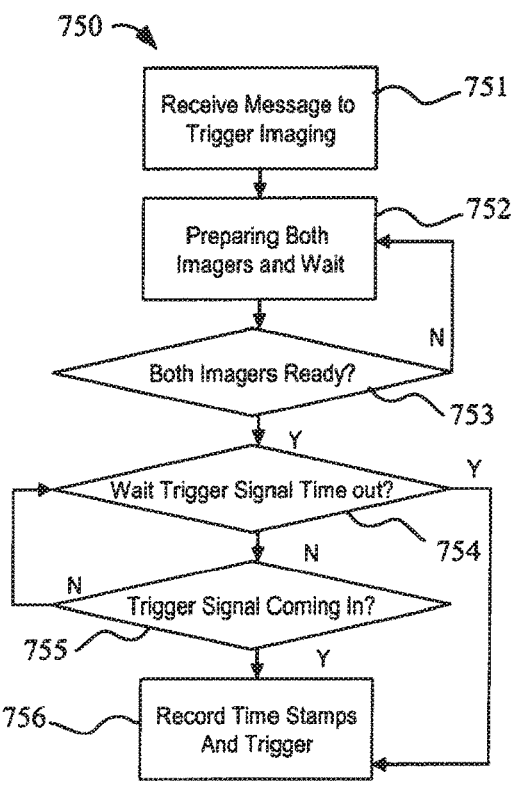
FIG. 7B illustrates a flow chart of one embodiment of automatically triggering acquisition of an image by automatically controlling the timing of the image acquisition.

FIG. 7B illustrates a flow chart of one embodiment of automatically triggering acquisition of an image by automatically controlling the timing of the image acquisition. Method 750 includes various operations to automatically control the timing of acquiring an image for a desired location of the respiratory cycle. The imaging system receives from the TLS a message to trigger imaging, operation 751. As described above, the message may be sent to the imaging system in response to an operation on the user interface. However, unlike operation 751, the imaging system does not acquire an image until a separate trigger signal (or command) based on a specified time in the respiratory cycle has been received, as described below. The imaging system prepares both imagers and waits, operation 752. The method 750 then determines if both imagers are ready, operation 753. If both imagers are not ready, the method 750 returns to operation 752. When both imagers are ready, the method 750 waits for a trigger signal (or command), and determines if a trigger signal timeout has occurred, operation 754. If the trigger signal timeout has not occurred, the method 750 determines if the trigger signal is coming from the TLS, operation 755. If the trigger signal has not been received, the method 750 operation returns to operation 754 to determine if the trigger timeout has occurred in operation 754. However, if the trigger signal has been received in operation 755, the imaging system records the time stamps and triggers the imagers to acquire the image, operation 756. The time stamps may be sent back to the TLS. However, if it is determined that the trigger timeout has occurred in operation 754, the imaging system records the time stamps and triggers the imagers to acquire the image, operation 756. When a timeout occurs the imagers still acquire an image, but it will not be at the designated time. In this embodiment, the trigger signal (or command) is sent on a communication channel between the TLS and the imaging system in real time at the desired times, which are determined by the TLS. The TLS calculates the desired time in the respiratory cycle to acquire the image for automatic modeling. The method 750 provides an automatic mechanism for the user to acquire substantially evenly-distributed model points for the correlation model, with minimal user interaction.

Figure 8A:
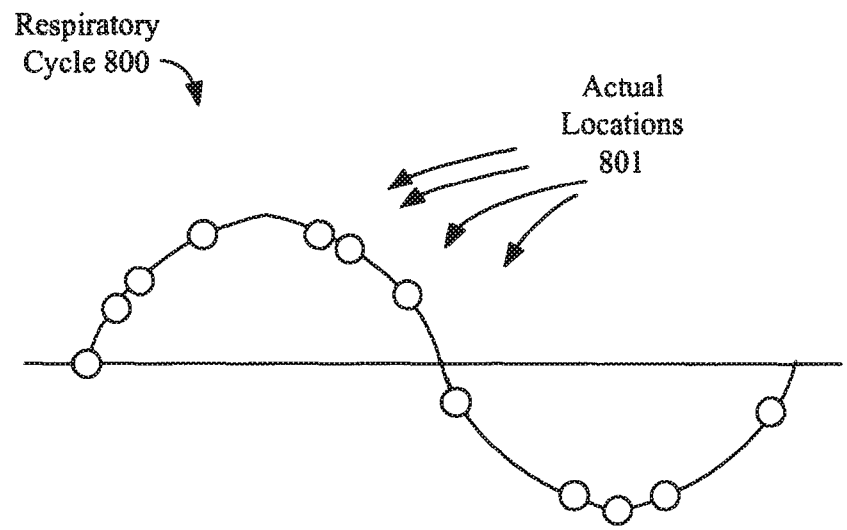
FIG. 8A illustrate exemplary model points of a respiratory cycle using the method of FIG. 7A.

FIG. 8A illustrate exemplary model points of a respiratory cycle 800 using the method of FIG. 7A. The respiratory cycle 800 includes multiple model points at the actual locations 801. The model points at the actual locations 801 represent the location in the respiratory cycle 800 at which the images were actually acquired using the manual timing process. Since the timing of the image acquisitions is manually controlled, the distribution of model points is not evenly distributed over the respiratory cycle 800. Also, it should be noted that in this example, more than eight model points are added to the model data set in an attempt to obtain model points at designated phases of the respiratory cycle, resulting in an increase of unnecessary imaging occurrences. Also, since the timing of the image acquisitions is manually controlled, the delay between when the operator manually triggers the imaging system and when the imaging system actually acquires the image, results in acquisition of model points at locations other than the desired locations 601, such as illustrated in FIG. 6. This delay complicates the guessing process to determine when, in the respiratory cycle, the operator should manually trigger the imaging system to acquire an image.

Figure 8B:
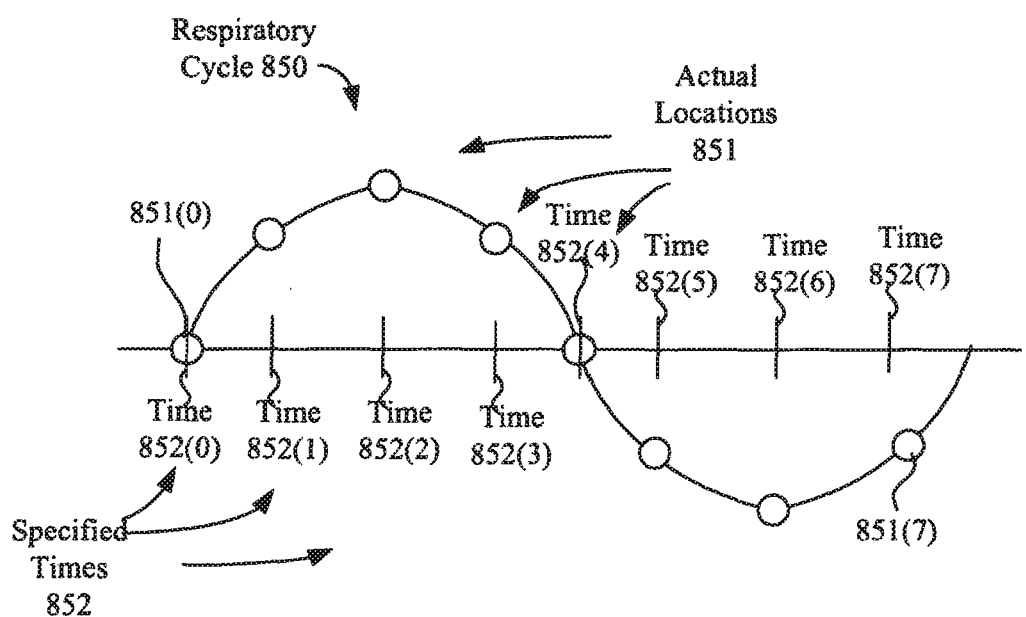
FIG. 8B illustrates one embodiment of an exemplary waveform having multiple model points at desired locations of a respiratory cycle using the method of FIG. 7B.

FIG. 8B illustrates one embodiment of an exemplary waveform having multiple model points at desired locations of a respiratory cycle 850 using the method of FIG. 7B. The respiratory cycle 850 includes multiple model points at the actual locations 851 at the specified times 852. The model points at the actual locations 851 represent the location in the respiratory cycle 850 at which the images were actually acquired using the automatic timing process. In this embodiment, the model points at the actual locations 851 are acquired at the specified times 852. For example, the model points at the actual locations 851(0)-851(7) are acquired at the specified times 852(0)-852(7), respectively. In this embodiment, the actual locations 851 of the model points correspond to the desired locations 601 (illustrated in FIG. 6), and the specified times 852 correspond to the desired times 602 (illustrated in FIG. 6). Since the timing of the image acquisitions is automatically controlled, the distribution of model points is substantially evenly distributed over the respiratory cycle 850, unlike the model points of the respiratory cycle 800. Also, it should be noted that in this embodiment, only eight model points are added to the model data set, and no more additional images are needed to obtain model points at designated phases of the respiratory cycle, unlike the example in FIG. 8A, since the eight images were acquired at the specified times 852 at the designated phases. As a result, there is not an increase in unnecessary imaging occurrences. Also, since the timing of the image acquisitions is automatically controlled, the delay between when the operator triggers the imaging system and when the imaging system actually acquires the image becomes irrelevant, since the system automatically controls the timing of the image acquisition at the desired location in the respiratory cycle 850. The system automatically controls the timing of the image acquisition at the specified time to obtain a model point at the desired locations 601 at the desired times 602 (illustrated in FIG. 6) in the respiratory cycle 600. By automatically controlling the time, the system can remove the guessing by the operator to determine when, in the respiratory cycle, the operator should manually trigger the imaging system to acquire an image.

Figure 9:
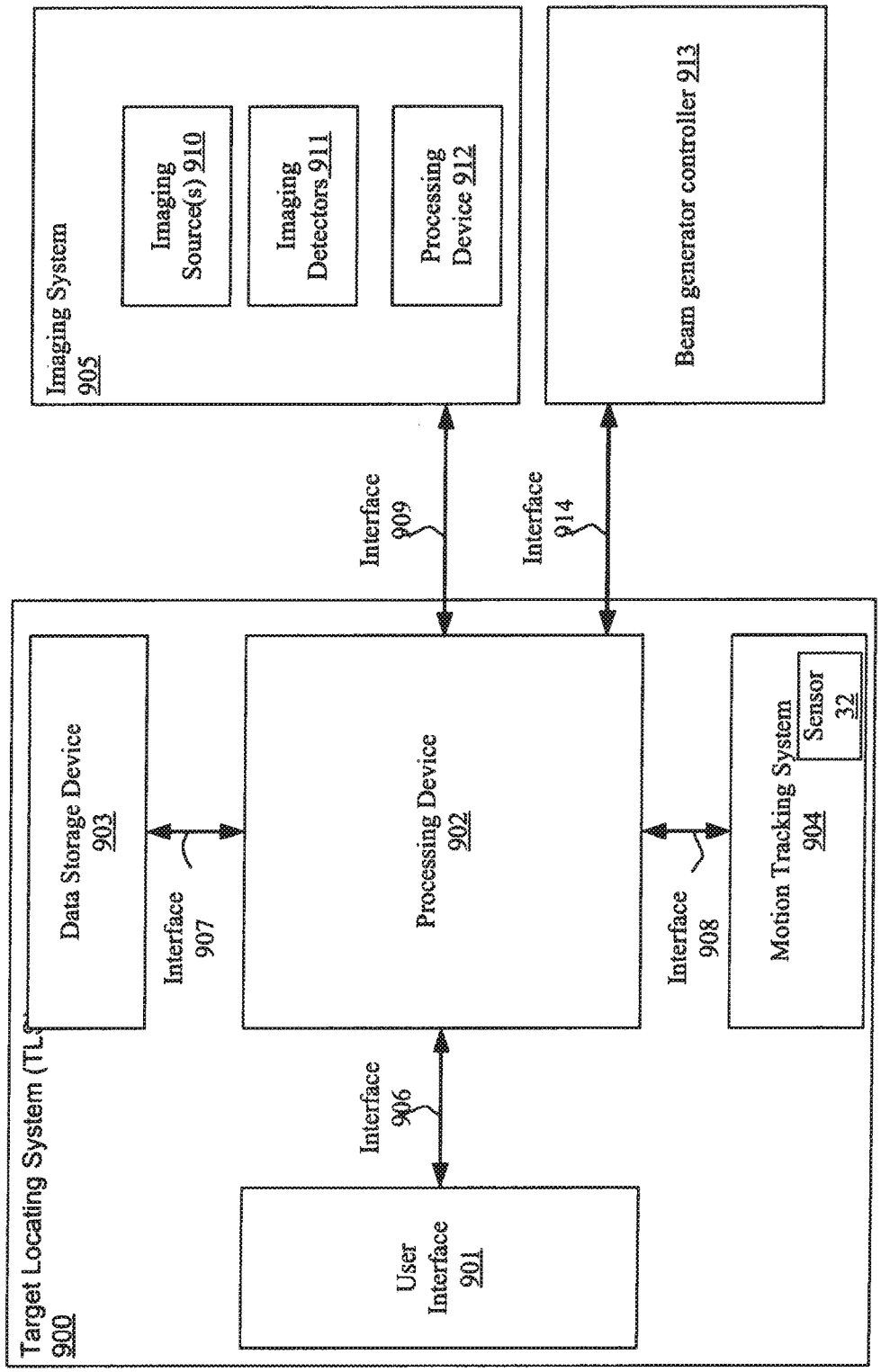
FIG. 9 illustrates a block diagram of one embodiment of a target locating system for automatic modeling.

FIG. 9 illustrates a block diagram of one embodiment of a target locating system 900 for automatic modeling. The target locating system 900 includes a user interface 901, a processing device 902, a data storage device 903, and a motion tracking system 904. The user interface 906, the data storage device 903, and the motion tracking system 904 are each coupled to the processing device 902 by interfaces 906, 907, and 908, respectively. The target locating system 900 is coupled to an imaging system 905 via interface 909. The imaging system 905 includes one or more imaging sources 910, one or more corresponding imaging detectors 911, and an image controller 912. The imaging sources 910, imaging detectors 911, and the image controller 912 are coupled to one another via a communication channel (not illustrated), such as a bus.

Figure 16:
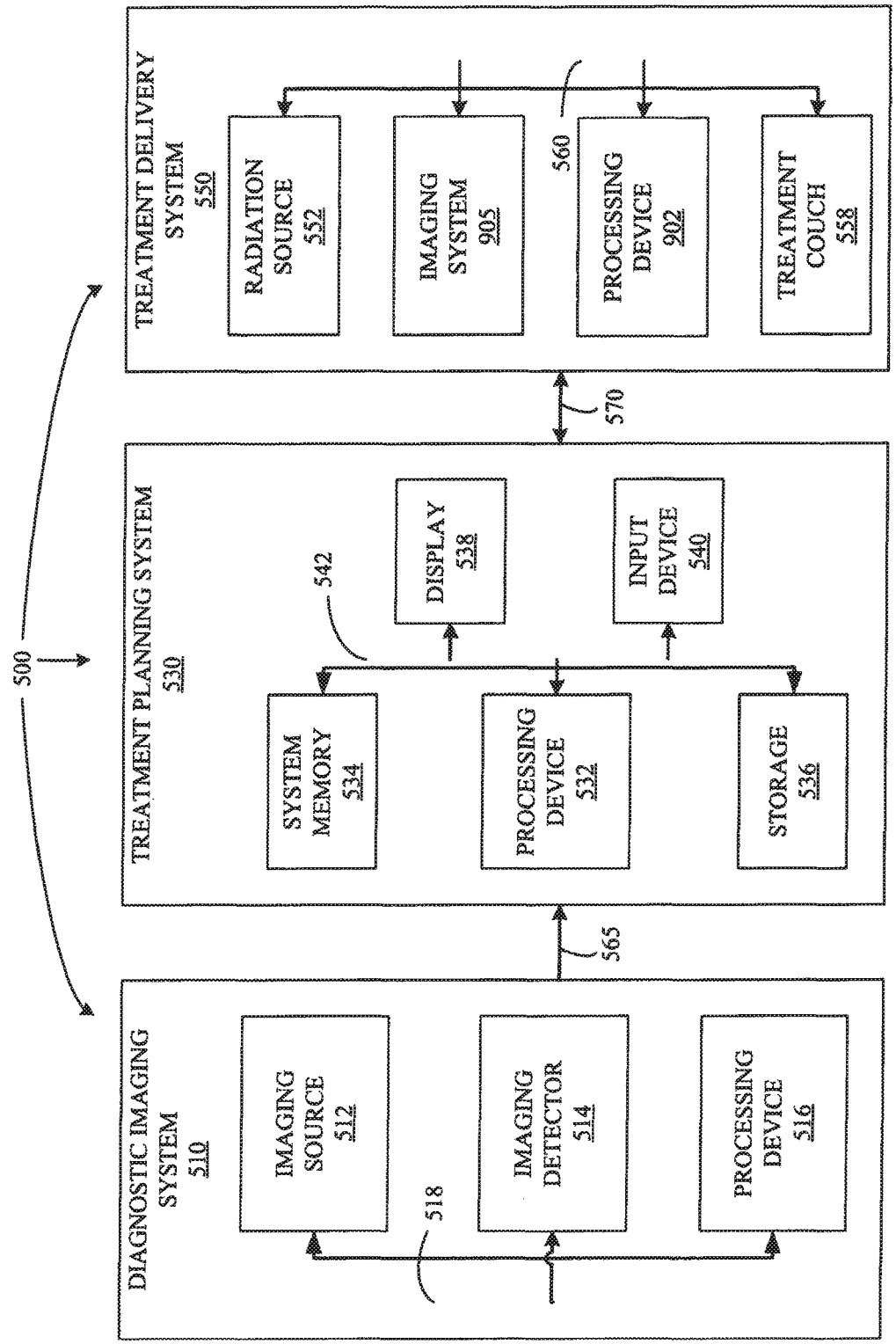
FIG. 16 illustrates one embodiment of a treatment system that may be used to perform radiation treatment in which embodiments of the present invention may be implemented.

The user interface 901 may include a display, such as display 538 described in FIG. 16, one or more input devices, such as keyboard, mouse, trackball, or similar device, to communicate information, to select commands for the processing device 902, to control cursor movements on the display, or the like. The user interface 901 is configured to help a user achieve automatic modeling with substantially evenly-distributed images of the target during the respiratory cycle with minimal user interaction. In one embodiment, the user interface 901 is a graphical user interface (GUI) that includes an "Acquire" button. Upon selecting the "Acquire" button, the user interface 901 sends an acquire command to the processing device 902. The processing device 902, in response, automatically determines the phases of the respiratory cycle at which to acquire images, and automatically triggers the imaging system 905 to acquire the images at determined specified times. In another embodiment, the user interface 901 provides a window with a generic graph of the respiratory cycle with multiple input devices (e.g., radio input buttons) to select a phase (e.g., location) of the respiratory cycle. The generic graph may appear similar to the waveform and model points of FIG. 6. In response, the processing device 902 automatically acquires the model point (e.g., image) at the indicated phase of the respiratory cycle. This may be repeated for other phases of the respiratory cycle. In another embodiment, the user interface 901 provides visual feedback of the positional data of the one or more external markers, actual locations of the respiratory cycle where images have been acquired, or the like. In another embodiment, the user interface 901 includes a button that automatically acquires the images at substantially evenly-distributed phases of the respiratory cycle, and automatically develops the correlation model based on the automatically acquired images. Alternatively, the user interface 901 may include more or less user-interface mechanisms than those described above to allow the user to interact with the target locating system 900 in automatically acquiring images at specified times.

In one embodiment, the imaging source 910 generates an imaging beam (e.g., X-rays, ultrasonic waves, radio frequency waves, etc.) and the imaging detector 911 detects and receives the imaging beam. Alternatively, the imaging detector 911 may detect and receive a secondary imaging beam or an emission stimulated by the imaging beam from the imaging source (e.g., in an MRI or PET scan). In one embodiment, the diagnostic imaging system 510 may include two or more diagnostic imaging sources 910 and two or more corresponding imaging detectors 911. For example, two X-ray sources 910 may be disposed around a patient to be imaged, fixed at an angular separation from each other (e.g., 90 degrees, 45 degrees, etc.) and aimed through the patient toward corresponding imaging detectors 911, which may be diametrically opposed to the imaging sources 911. A single large imaging detector 911, or multiple imaging detectors 911, also may be illuminated by each X-ray imaging source 911. Alternatively, other numbers and configurations of imaging sources 910 and imaging detectors 911 may be used.

The imaging source 910 and the imaging detector 911 are coupled to the image controller 912, which controls the imaging operations and process image data within the imaging system 905. In one embodiment, the processing device 516 communicates with the imaging source 512 and the imaging detector 514. Embodiments of the processing device 516 may include one or more general-purpose processors (e.g., a microprocessor), special purpose processors such as a digital signal processor (DSP), or other type of devices such as a controller or field programmable gate array (FPGA). The processing device 516 also may include other components (not shown) such as memory, storage devices, network adapters, and the like. In one embodiment, the processing device 516 generates images (e.g., diagnostic and/or intra-treatment images) in a standard format such as the Digital Imaging and Communications in Medicine (DICOM) format. In other embodiments, the processing device 516 may generate other standard or non-standard digital image formats.

The motion tracking system 904 is configured to track and compensate for the motion of the target 10 with respect to the radiation source of the LINAC 20 (not illustrated in FIG. 9). The motion tracking system 904 includes one or more tracking sensors 32 that track the location of one or more external markers 25. For example, the tracking sensor 32 may track upward movement of the external marker 25 during the inspiration interval and downward movement of the external marker 25 during the expiration interval. The relative position of the external marker 25 is correlated with the location of the target 10, so that the LINAC 20 may move relative to the location of the external marker 25 and the correlated location of the target 10. In another embodiment, other types of external or internal markers may be used instead of, or in addition to, the illustrated external marker 25.

As one example, the depicted target 10 is shown four positions designated as $D_0$, $D_3$, $D_5$, and $D_7$, as illustrated and described with respect to FIG. 1. As the patient breathes, the target 10 may move along a path within the patient's body. In one embodiment, the path of the target 10 is asymmetric in that the target 10 travels along different paths during the inspiration and expiration intervals. In another embodiment, the path of the target 10 is at least partially non-linear. The path of the target 10 may be influenced by the size and shape of the target 10, organs and tissues surrounding the target 10, the depth or shallowness of the patient's breathing, and so forth. By correlating the positions of the external marker 25 to the target 10, the position of the target 10 may be derived from the position of the external marker 25 even though the external marker 25 may travel in a direction or along a path that is substantially different from the path and direction of the target 10. The LINAC 20 is also shown in a first position, $D_0$, a second position, $D_3$, a third position, $D_5$, and a fourth position, $D_7$, which also correspond to the positions of the target 10, as described and illustrated with respect to FIG. 1. In this way, the movements of the LINAC 20 may be substantially synchronized to the movements of the target 10 as the position of the target 10 is correlated to the sensed position of the external marker 25.

Tracking the position of the target 10 using motion tracking system 904 may be performed in a number of ways. Some exemplary tracking technologies include fiducial tracking, soft-tissue tracking, and skeletal structure tracking, which are known in the art; accordingly, a detailed discussion is not provided.

In one embodiment, the motion tracking system 904 is the SYNCHRONY® respiratory tracking system, developed by Accuray, Inc., Sunnyvale, Calif. Alternatively, other motion tracking systems may be used.

In one embodiment, the motion tracking system 904 is used in conjunction with the processing device 902 of the treatment delivery system 900 to deliver radiation beams to a target whose surrounding tissue is moving with respiration during treatment delivery. The motion tracking system 904 tracks motion of one or more external markers (not illustrated in FIG. 9) that are disposed on the patient. The motion tracking system 904 also is configured to compensate for the motion of the target immediately before or during treatment delivery. In compensating for the motion of the target, motion tracking system 904 determines the movement of the one or more external marker over time. The movement of the one or more external markers may be sent to the processing device 902 for processing and to the storage device 903 to be stored in a data set for the correlation model. In one embodiment, the LINAC 20, which includes the radiation source 106, is moved to compensate for the motion of the target 10, as determined by the TLS 900. For example LINAC 20 may move to keep the source-to-axis (SAD) fixed, based on the calculations made by the motion tracking system 904 or the processing device 902. Alternatively, the LINAC 20 is stationary, and the motion tracking system 904 determines a different value for the SAD.

In one embodiment, the data storage device 903 stores multiple displacement points of the monitored, external marker. The displacement points are indicative of the motion of the external marker during a respiratory cycle of a patient. The processing device 902 determines a specified time in the respiratory cycle that corresponds to a first phase of the respiratory cycle to acquire an image of a target based on the stored displacement points. The processing device 902 also automatically triggers the imaging system 905 to acquire the image of the target at the first phase of the respiratory cycle. The processing device 902 also determines additional specified times in the same or subsequent respiratory cycles as the first specified time, to acquire additional images of the target, corresponding to other phases of the respiratory cycle, and automatically triggers the imaging system to acquire the additional images of the target at the specified times to obtain model points that correspond to the other phases of the respiratory cycle. In addition to storing the displacement points, the storage device 903 may be configured to store the image data of the images acquired by the imaging system 905. The processing device 902 uses the images and the displacement points to generate the correlation model.

It should be noted that in the embodiment above, the different phases of the respiratory cycle are substantially evenly distributed, and since the timing of the image acquisition is automatically controlled by the processing device 902, the acquired images, which serve as model points for the model correlation, are substantially evenly distributed, resulting in a better correlation model than a correlation model with unsubstantially evenly-distributed model points.

In another embodiment, the imaging system 905, under control of the processing device 902 or image controller 912, periodically generates positional data about the target by automatically acquiring images of the target during treatment, and the motion tracking system 904 continuously generates positional data about the external motion of the one or more external markers during treatment. The positional data about the target and the positional data about the external motion of the external marker are used to update the correlation model. The timing of the image acquisition of the images during treatment may also be automatically controlled by the processing device 902 so that the images are acquired at specified times (corresponding to specified phases) of the respiratory cycle. In one embodiment, the correlation model is generated immediately before treatment using pretreatment images acquired by the imaging system 905 at the specified times and displacement points acquired by the motion tracking system 904. During treatment, a current position of the target is determined using the correlation model. Additional images and displacement points may be acquired, and the correlation model is updated based on the additional images and displacement points.

In one embodiment, in order to automatically acquire images at specified times, the processing device 902 sends a trigger command or signal to the imaging system 905 on interface 909. The trigger command may be in addition to a command or signal sent by the processing device 902 to the imaging system 905 to prepare the imaging sources 910 for image acquisition. Once the imaging system 905 is ready to acquire an image, the imaging system 905 waits to receive the trigger command or signal to actually acquire an image. By using the trigger command or signal, the processing device 210 can automatically control the timing of the image acquisition by the imaging system 905 to be performed at specific times in the respiratory cycle.

The processing device 210 is also configured to derive a target position of the target based on the correlation model, and to send a position signal associated with the target position to a beam generator controller 913, which controls the radiation source of the LINAC 20 to direct a beam at the target, via an interface 914. In this way, the movements of the LINAC 20 may be substantially synchronized to the movements of the target 10 as the position of the target 10 is correlated to the sensed position of the external marker 25.

In another embodiment, the processing device 902 is part of the motion tracking system 904 and interfaces with the imaging system 905 to automatically control the timing of acquisitions of the images, as described above. Alternatively, other configurations of the processing device 902, motion tracking system 904, and the imaging system 905 may be used.

Figure 10:
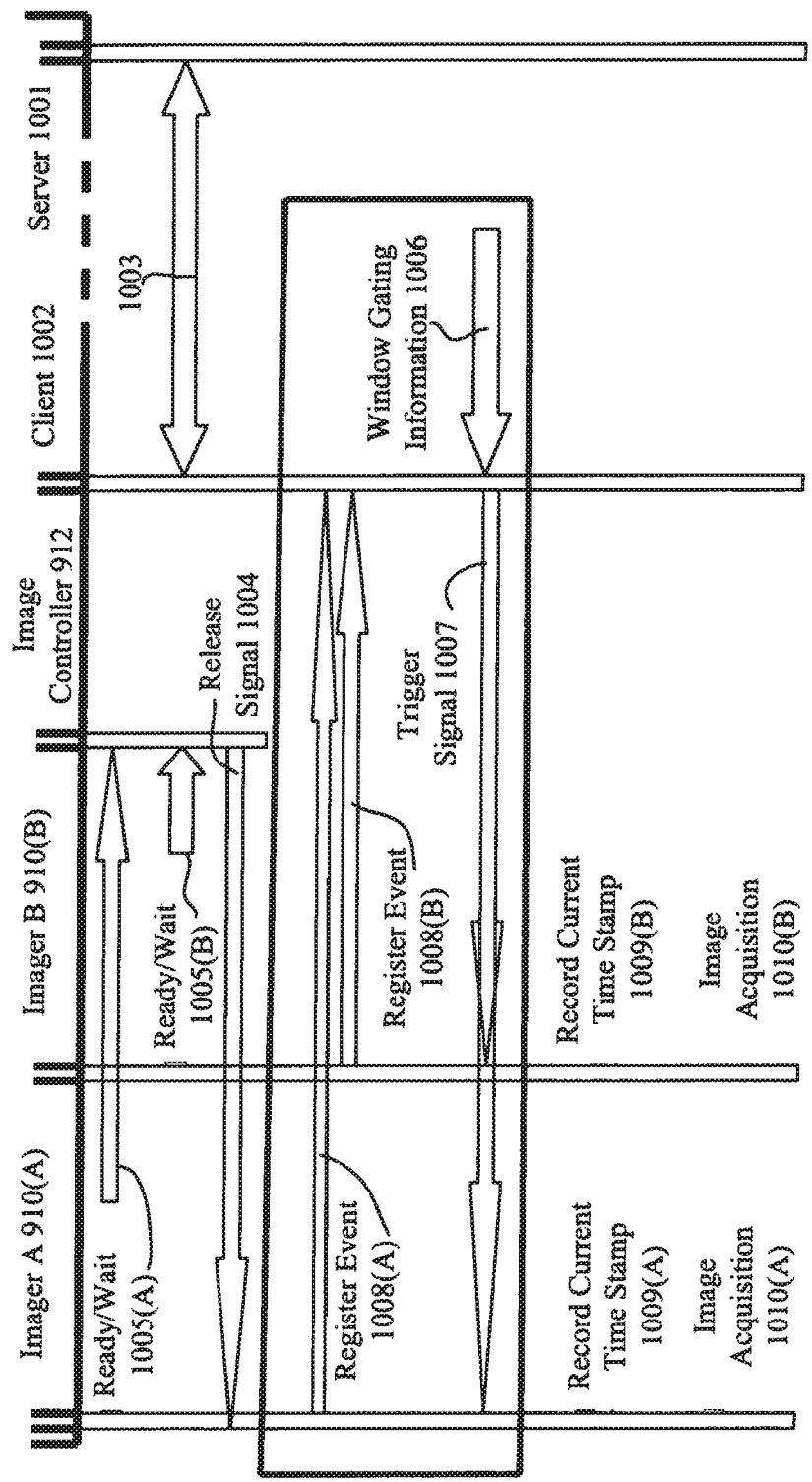
FIG. 10 illustrates a separate processing thread on a client for automatic modeling in a client-server environment according to one embodiment of the invention.

FIG. 10 illustrates a separate processing thread 1000 on a client 1002 for automatic modeling in a client-server environment according to one embodiment of the invention. An automatic modeling client is running in the separate thread 1000 on the client 1002 to provide automatic control of the timing of image acquisition. The server 1001, which may be the target location system 900, interacts with the client 1002, which may be the imaging system 905. The server 1001 and client 1002 interact with communications 1003 over an interface, such as interface 909, described above. For example, the server 1001 sends a message to the client 1002 to automatically acquire one or more images at specified times in the respiratory cycle. The client 1002, in response to the message in the communication 1003, the image controller 912 sends release signals (or commands) 1004 to the imager A 910(A) and to the imager B 910(B), such as described above with respect to operation 752 of FIG. 7B. The imagers 910(A) and 910(B) prepare to acquire images, and when each of the imagers 910(A) and 910(B) are ready, a ready/wait signal (1005(A) and 1005(B)) are sent to the image controller 912 to indicate that each of the imagers 910(A) and 910(B) are ready to acquire an image. Unlike the method 700, described above, the imagers 910(A) and 910(B) do not acquire an image at this point, but wait until a separate trigger signal 1007 has been received from the imaging controller 912. The separate trigger signal 1007 allows the image acquisition to be performed at a specified time in the respiratory cycle, as described herein. In this embodiment, the client 1002 receives window gating information 1006 to determine when to issue the trigger signal 1007. The window gating information 1006 may include the external marker analysis (e.g., LED analysis) that includes an imaging window to allow the image controller 912 to issue the trigger signal 1007 within the imaging window. By imaging in the imaging window, an image may be acquired at the specified location in the respiratory cycle. In response to the trigger signal 1007, the imagers 910(A) and 910(B) record the current time stamp 1009(A) and 1009(B) and perform the image acquisitions 1010(A) and 1010(B) to acquire an image at the specified time. The imagers 910(A) and 910(B) also register the event 1008(A) and 1008(B) with the image controller 912, as part of the separate thread 1000.

The separate thread 1000, including the trigger signal 1007, is used to automatically control the timing of image acquisition by the imagers 910(A) and 910(B) at the specified time. By automatically controlling the timing, images may be acquired at substantially evenly-distributed phases of the respiratory cycle.

In another embodiment, the window gating information 1006 is determined by the server 1001 and the server sends the window gating information 1006 to the client 1002 regarding the imaging window in which to acquire an image. In another embodiment, the image controller 912 receives raw data of the external marker and determines the imaging window to acquire the image at a specific time in the respiratory cycle.

Although the server 1002 is described as being the target locating system 900, alternatively, the server 1002 may be the motion tracking system 904, or other systems that can determine the window gating information 1006 for the client 1002.

Figure 11:
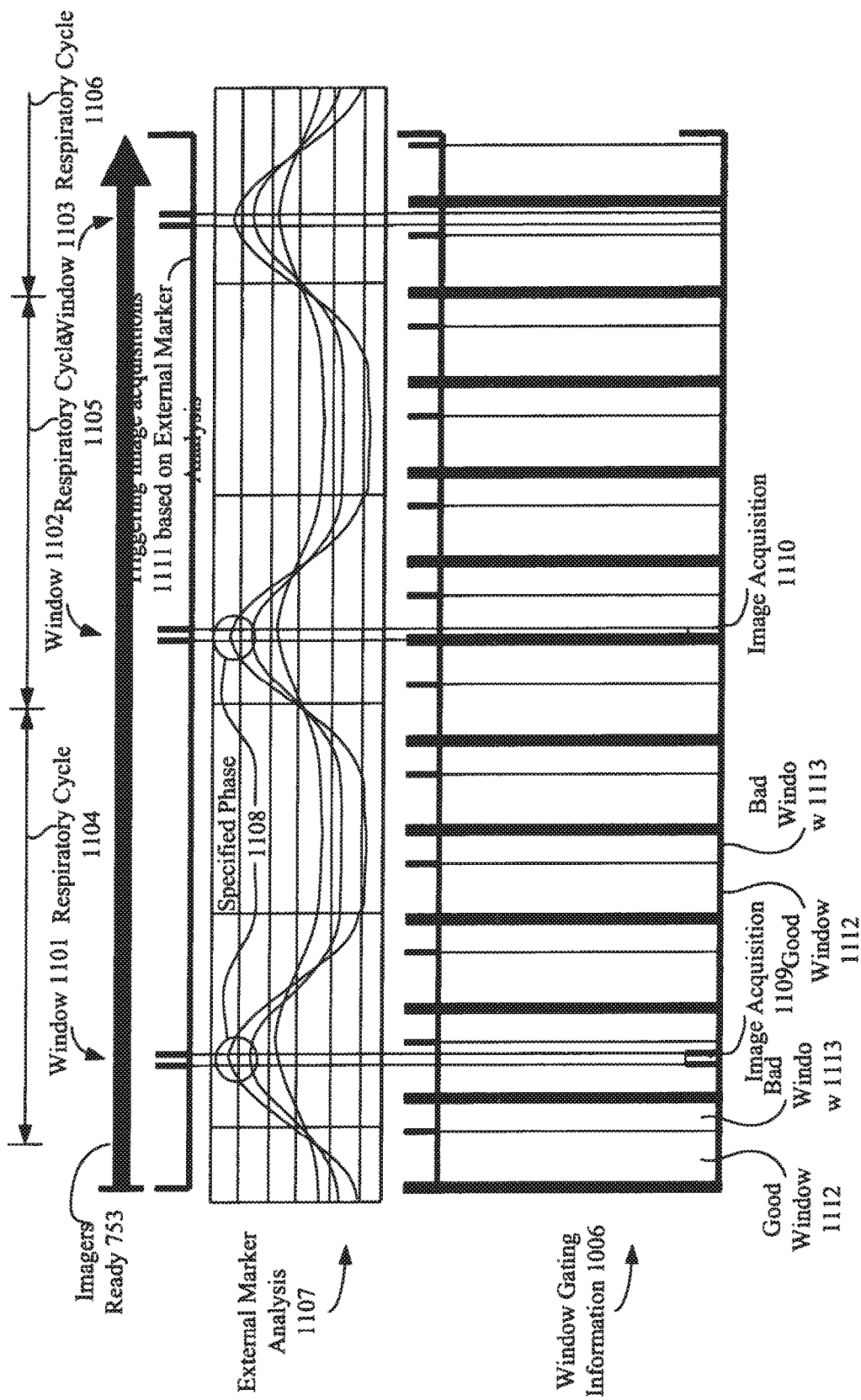
FIG. 11 illustrates windows for automatically triggering image acquisition at a specified phase of the respiratory cycle according to one embodiment of the invention.

FIG. 11 illustrates windows for automatically triggering image acquisition at a specified phase of the respiratory cycle according to one embodiment of the invention. When both imagers 910(A) and 910(B) are ready, such as in operation 753 of FIG. 7B, external marker analysis 1107 may be used to determine the window gating information 1006, as described above, for triggering image acquisitions 1111 based on the external marker analysis 1107. The window gating information 1006 is used to determine an imaging window (e.g., window 1101-1103) to trigger image acquisition at a specified phase 1108 of the respiratory cycle. The window gating information 1006 may also include information on good and bad windows 1112 and 1113 (not all labeled), respectively, which indicate whether a window is a good or bad window in which to acquire an image based on the external marker analysis 1107. The external marker analysis 1107 includes positional data about three external markers. The positional data about the three external markers define the respiratory cycles 1104-1106. Using the positional data, the system (e.g., processing device 902) can either automatically select a specified phase 1108 at which to acquire an image, or the system can allow a user to select the specified phase 1108. Once the specified phase 1108 has been selected, the system determines the windows 1101-1103 at which the imagers 910(A) and 910(B) should acquire an image for the specified phase 1108. Since the imagers 910(A) and 910(B) are ready, the imagers 910(A) and 910(B) can receive a trigger signal in the window 1103, and each acquire an image (e.g., image acquisition 1109) during the window 1103, which is designated as a good window 1112 for the specified phase 1108. If the images are not acquired in the window 1103, the imagers 910(A) and 910(B) can receive a trigger signal in the window 1104, and each acquire an image (e.g., image acquisition 1110) during the window 1104, which is designated as a good window 1112 for the specified phase 1108. Similarly, if the images are not acquired in the window 1104, the images may be acquired in the window 1105, which is also designated as a good window 1112 for the specified phase 1108. Each of the windows 1103-1105 represents good windows 1112 for the specified phase 1108. As such, an image can be automatically acquired at the specified time and location of the respiratory cycle.

Figure 12:
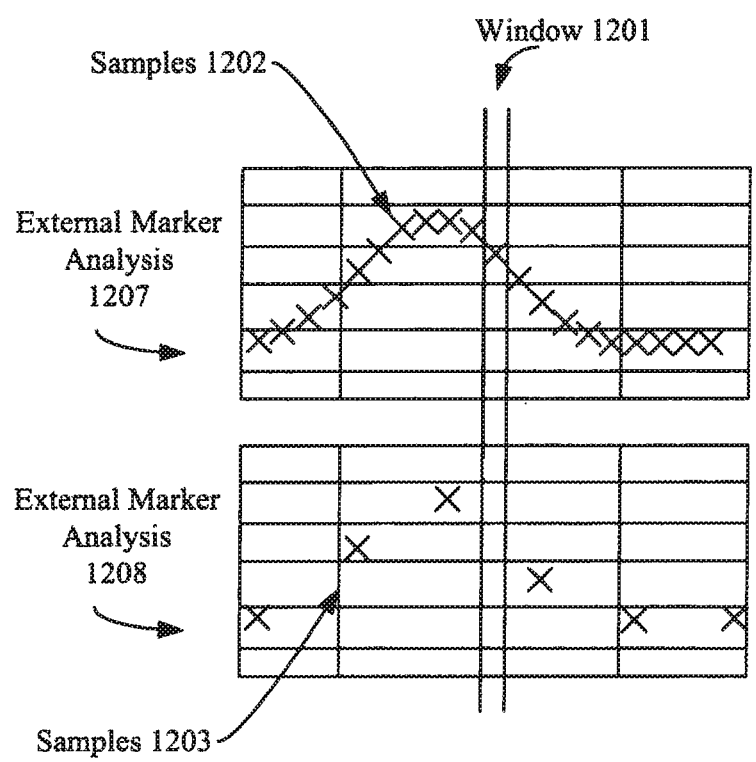
FIG. 12 illustrates two embodiments of automatically triggering image acquisition at a specified time of the respiratory cycle during a window.

FIG. 12 illustrates two embodiments of automatically triggering image acquisition at a specified time of the respiratory cycle during a window 1201. As described above, when the both imagers 910(A) and 910(B) are ready, the external marker analysis 1207 is used to determine the window 1201, in which to acquire the image. In one embodiment, the external marker analysis 1207 is sampled at a rate that is substantially higher than the frequency of the respiratory cycle to allow the samples 1202 to represent real time, or near real time information on when to trigger the imagers 910(A) and 910(B). Each update of the sample represents a potential point to trigger the imagers 910(A) and 910(B). According to the pattern of the samples 1202, the desired phase (e.g., window 1201) can be estimated using updated samples 1202. If in the current location of the samples 1202 is desired to acquire an image (e.g., within window 1201), the imaging message is issued to that imagers 910(A) and 910(B) to trigger X-ray imaging.

In the other embodiment, the sampling rate of the external marker analysis 1208 is lower than the sampling rate of the external marker analysis 1207. Since the sampling rate of the external marker analysis 1208 is lower, the timing for image acquisition may need to be predicted. For example, using the pattern of the external marker analysis 1208, the window 1201 may be predicted by interpolating the samples 1208 to determine the window 1201 to trigger image acquisition. It should be noted that in these embodiments, the X-ray firing is not an instant reaction after triggering, but is a delayed-response triggering. The samples 1203 are used to predict a time at which to acquire the image between samples 1208. The prediction is based on the estimated respiratory period, as illustrated in the external marker analysis 1208, and a nominal delay after the last sample 1203. Using a prediction allows automatic image acquisition at specified times (e.g., window 1201) during the respiratory cycle, regardless of whether the sampling rate of the external markers is updated in real time or less than real time.

In one embodiment, historical data 1302 is represented in a historical data window that is configured to move forward adaptively in time. Each update of the historical data (e.g., each sample of the LED movement), the system updates the historical data window by re-evaluating the historical data 1302.

Figure 13:
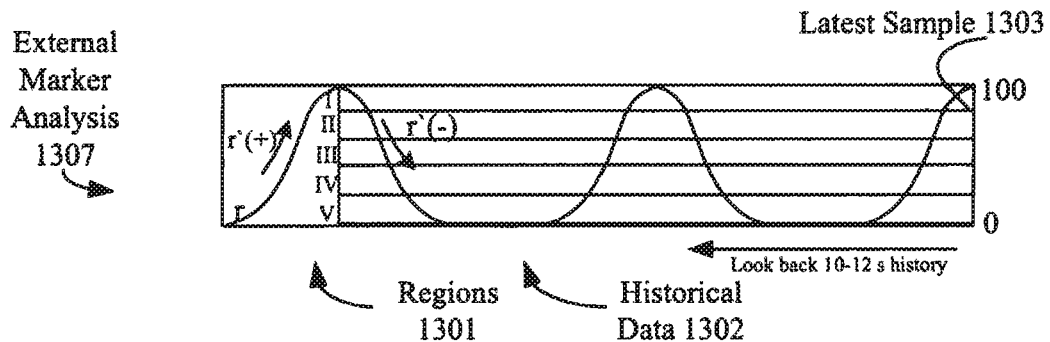
FIG. 13 illustrates one embodiment of determining a specified time for image acquisition.
Figure 13:
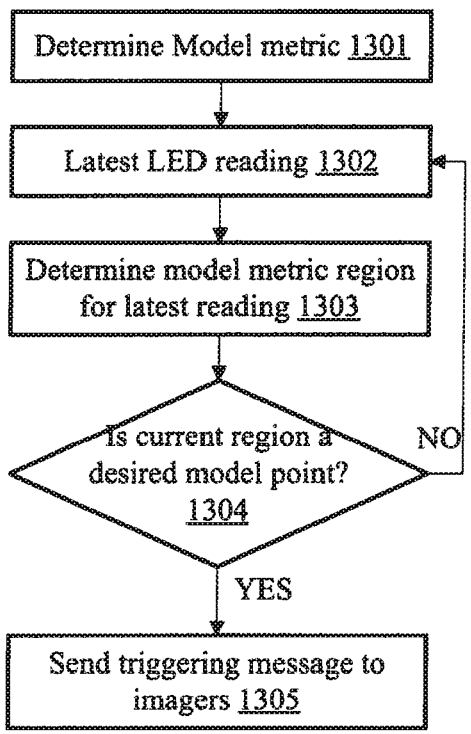

FIG. 13 illustrates one embodiment of determining a specified time for image acquisition. In this embodiment, a model metric is determined by (1301), first, gathering historical sample data 1302 (e.g., 10-12 seconds) that precedes the latest sample 1303, and second, evenly divide the sample data into five regions 1301 of motion range. The five regions 1301 represent the range of motion (r) (e.g., LED movement waveform) during that portion of the respiratory cycle, and the five regions 1301 are scaled between 0 and 100 based on the minimum and the maximum, 0 being assigned to the minimum and 100 being assigned to the maximum. In this embodiment, the region I is between 80 and 100, region II is between 60 and 80, region III is between 40 and 60, region IV is between 20 and 40, and region V is between 0 and 20. Next, the range of motion is distinguished for inspiration and expiration using the derivative r', indicated by r'(+) and r'(−) for inspiration and expiration, respectively, or vice versa. The latest sample 1303 can then be categorized into the following table of eight model metric regions:

TABLE 3

Model Metric Regions.

1) I ($r' \approx 0$)
2) II ($r'(+)$)
3) III ($r'(+)$)
4) IV $r'(+)$
5) V ($r' \approx 0$)
6) II ($r'(-)$)
7) III ($r'(-)$)
8) IV ($r'(-)$)

The eight model metric regions correspond to the eight phases of the respiratory cycle. In one embodiment, an image is acquired for each of the eight phases of the respiratory cycle.

Once the model metric regions have been determined in operation 1301, the system determines the latest LED reading (e.g., latest sample 1303), in operation 1302, and determines in which of the eight model metric region it belongs using r and r', operation 1303. Next, the system determines if the current location of the latest sample 1303 is a desired model point for the correlation model, operation 1304. If the current location is not a desired model point, the system returns to obtaining the latest LED reading in operation 1302. However, if the current location is a desired model point, the system sends a triggering message (e.g., triggering signal or command) to automatically trigger the imagers 910(A) and 910(B) to take an image, operation 1305.

It should be noted that although the embodiment of described using five regions, alternatively, more or less regions may be used to categorize the range of motion into various model metric regions. Also, in another embodiment, the system can determine a delay in which to acquire an image between sample points for delayed-response triggering, as described above.

Figure 14:
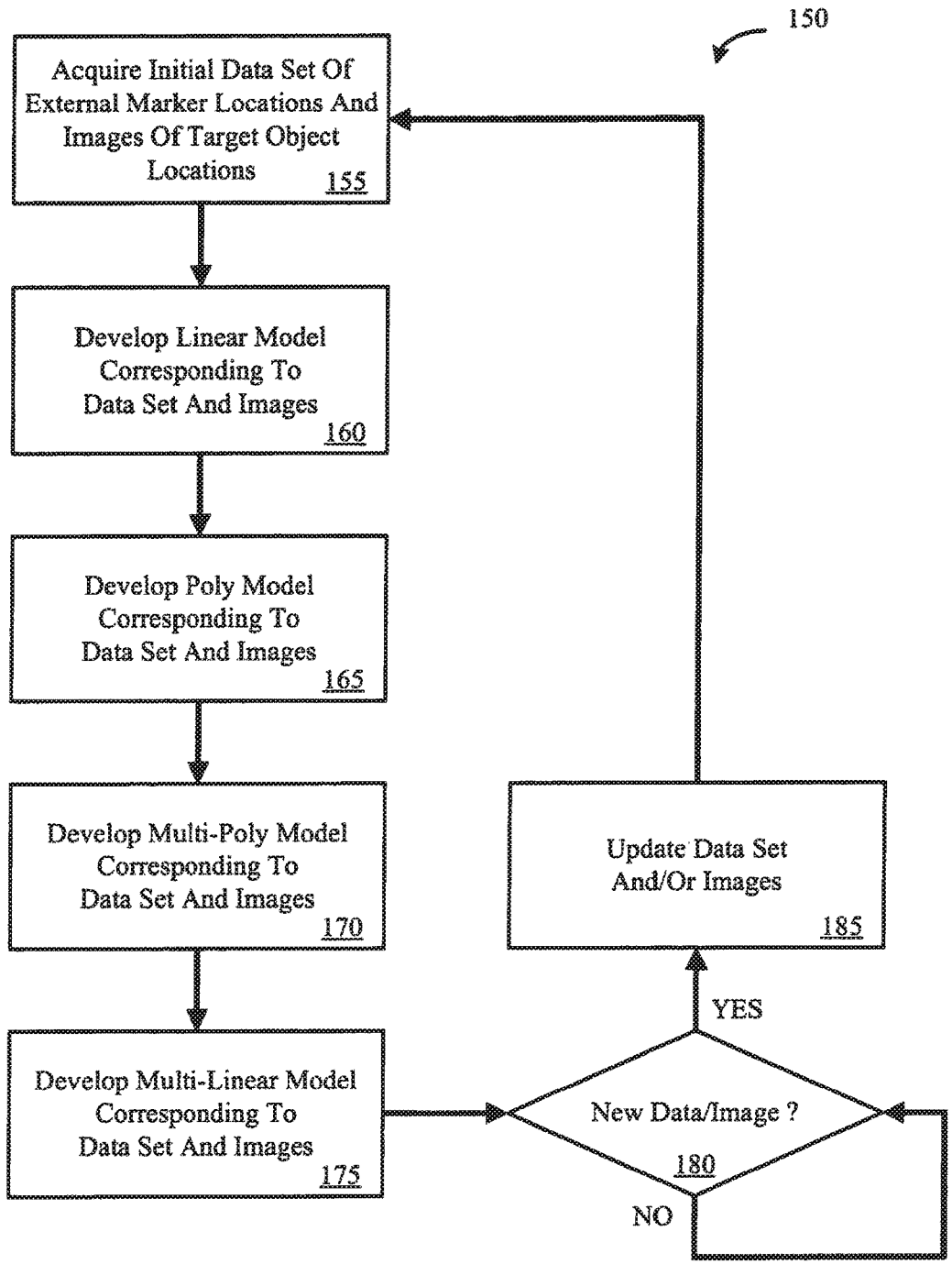
FIG. 14 illustrates one embodiment of a modeling method.

FIG. 14 illustrates one embodiment of a modeling method 150. In one embodiment, the modeling method 150 may be implemented in conjunction with a treatment system such as the treatment system 500 of FIG. 16. Furthermore, the depicted modeling method 150 may be implemented in hardware, software, and/or firmware on a treatment system 500, such as the treatment planning system 530 or the treatment delivery system 550. Although the modeling method 150 is described in terms of the treatment system 500, embodiments of the modeling method 150 may be implemented on another system or independent of the treatment system 500. In one embodiment, the depicted modeling method 150 is implemented in hardware, software, and/or firmware on a treatment planning system, such as the treatment planning system 530 of FIG. 16. Although the modeling method 150 is described in terms of the treatment planning system 530, embodiments the modeling method 150 may be implemented on another system or independent of the treatment planning system 530.

The illustrated modeling method 150 begins and the treatment planning system 530 acquires an initial data set of locations of an external marker 25, operation 155. As part of operation 155, the treatment planning system 530 also automatically acquires 155 one or more images of the target 10. It should be noted that these images are automatically acquired at specified times (corresponding to specified phases) of the respiratory cycle, as described herein. The location of the target 10 may be derived from these images. The position of the target 10 also may be determined relative to the location of the external marker 25.

The treatment planning system 530 subsequently uses the data set and images to develop a linear correlation model as described above, operation 160. The treatment planning system 530 also uses the data set and images to develop a nonlinear polynomial correlation model as described above, operation 165. The treatment planning system 530 also uses the data set and images to develop a multi-poly correlation model as described above, operation 170. The treatment planning system 530 also uses the data set and images to develop a multi-linear correlation model, operation 175. The multi-linear correlation model includes a linear model for the inspiration and a linear model for the expiration. Although the illustrated modeling method 150 develops several types of correlation models, other embodiments of the modeling method 150 may develop fewer or more correlation models, including some or all of the correlation models described herein. The different types of correlation models are known to those of ordinary skill in the art, and additional details regarding these types of correlation models have not been included so as to not obscure the embodiments of the present invention.

The treatment planning system 530 maintains these correlation models and, in certain embodiments, monitors for or acquires new data and/or images. When new data or images are received, operation 180, the treatment planning system updates the data set and or the images, operation 185, and may iteratively develop new models based on the new information. In this way, the modeling method 150 may maintain the correlation models in real-time.

It should be noted that the method 150 may also be performed in the treatment delivery system 550 described with respect to FIG. 16, or the target locating system described with respect to FIG. 9.

As part of the method in another embodiment, the treatment planning system 530 determines if the displacement of the external marker 25 is within the boundaries of the various correlation models. For example, many of the correlation models described above have a displacement range between approximately zero and 30 mm. A patient may potentially inhale or exhale in a way that moves the external marker 25 outside of a correlation model range. If the displacement of the external marker 25 is not within the range of the correlation models, then the treatment planning system 530 may select the linear correlation model and extrapolate outside of the model boundaries. Alternatively, the treatment planning system 530 may select another correlation model such as the multi-linear correlation model and determine an estimated location of the target 10 from the selected correlation model.

Figure 15:
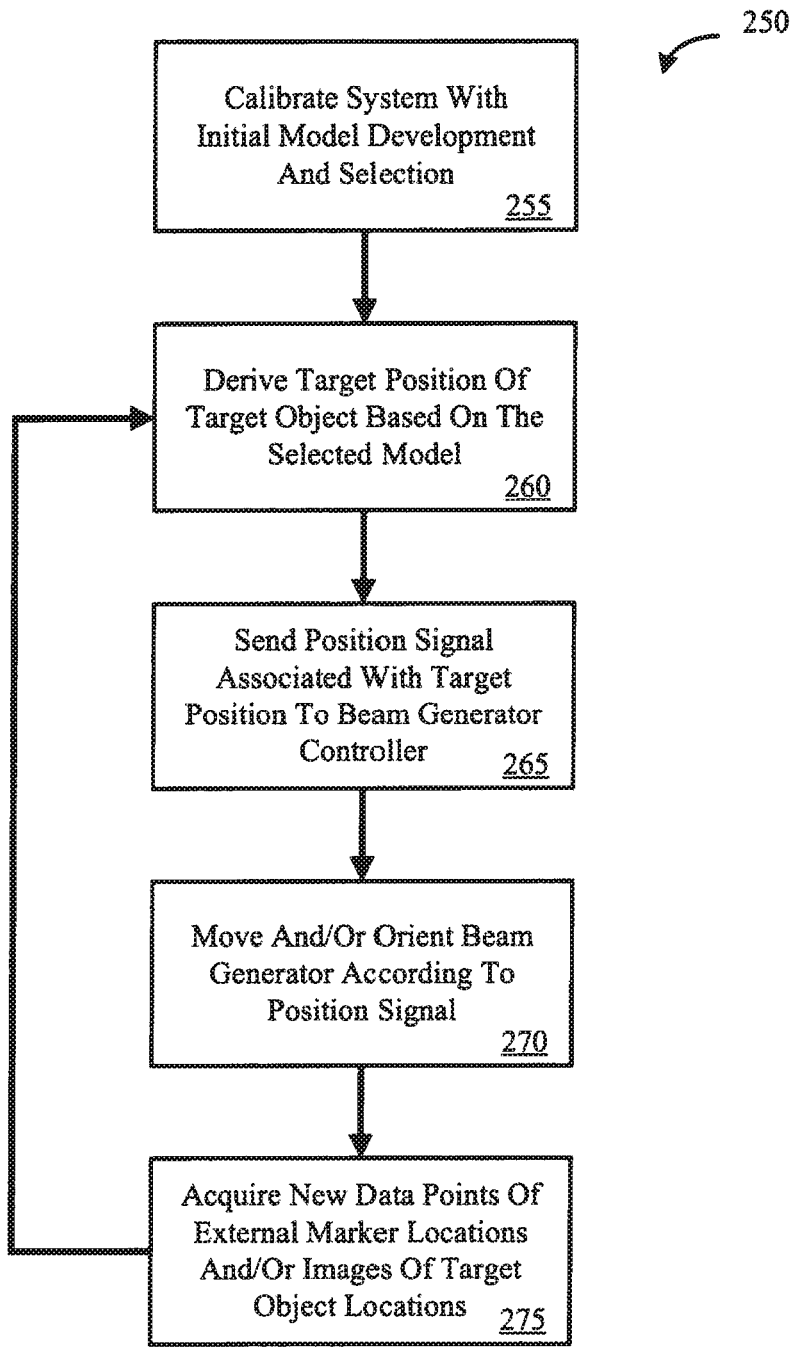
FIG. 15 illustrates one embodiment of a tracking method.

FIG. 15 illustrates one embodiment of a tracking method 250. In one embodiment, the tracking method 250 is implemented in conjunction with a treatment system such as the treatment system 500 of FIG. 16. Furthermore, the depicted tracking method 250 may be implemented in hardware, software, and/or firmware on a treatment system 500. Although the tracking method 250 is described in terms of the treatment system 500, embodiments of the tracking method 250 may be implemented on another system or independent of the treatment system 500.

The illustrated tracking method 250 begins and the treatment system 500 performs calibration to initialize model development and selection, operation 255. In one embodiment, such calibration includes performing the modeling method 150 prior to treatment delivery. In another embodiment, the modeling method 150 is performed multiple times to establish historical data.

After the tracking system 500 is calibrated, the tracking system 500 derives a target position of the target 10 based on the selected correlation model, operation 260. As described above, the target location of the target 10 may be related to the known position of the external marker 25 and derived from one of the correlation models. The tracking system subsequently sends a position signal indicating the target position to a beam generator controller (e.g., beam generator controller 913 of FIG. 9), operation 265. In one embodiment, the treatment system 500 delivers the position signal to a treatment delivery system, such as the treatment delivery system 550 of FIG. 16. The treatment delivery system 550 then moves and orients the beam generator, such as the radiation source 552 of FIG. 16, operation 270. The treatment delivery system 550 and radiation source 552 are described in more detail below.

The treatment planning system 530 continues to acquire new data points of the external marker 25 and new images of the target 10 at a random phase or a specified phase of the respiratory cycle, operation 275. In one embodiment, the treatment planning system 530 may repeatedly develop models according to the modeling method 150 and select a model, as described above. In another embodiment, the treatment planning system 530 may select and use one model to derive multiple target positions. The tracking method 250 may continue in this manner of developing one or more models, selecting a model, and delivering treatment according to the selected model for the duration of a treatment session.

FIG. 16 illustrates one embodiment of a treatment system 500 that may be used to perform radiation treatment in which features of the present invention may be implemented. The depicted treatment system 500 includes a diagnostic imaging system 510, a treatment planning system 530, and a treatment delivery system 550. In other embodiments, the treatment system 500 may include fewer or more component systems.

The diagnostic imaging system 510 is representative of any system capable of producing medical diagnostic images of a volume of interest (VOI) in a patient, which images may be used for subsequent medical diagnosis, treatment planning, and/or treatment delivery. For example, the diagnostic imaging system 510 may be a computed tomography (CT) system, a magnetic resonance imaging (MRI) system, a positron emission tomography (PET) system, an ultrasound system, or another similar imaging system. For ease of discussion, any specific references herein to a particular imaging system such as a CT X-ray imaging system is representative of the diagnostic imaging system 510, generally, and does not preclude other imaging modalities, unless noted otherwise. In one embodiment, the diagnostic imaging system 510 is similar to the imaging system 905, described with respect to FIGS. 9 and 14. In another embodiment, the diagnostic imaging system 510 and the imaging system 905 are the same imaging system.

The illustrated diagnostic imaging system 510 includes an imaging source 512, an imaging detector 514, and a processing device 516. The imaging source 512, imaging detector 514, and processing device 516 are coupled to one another via a communication channel 518 such as a bus. In one embodiment, the imaging source 512 generates an imaging beam (e.g., X-rays, ultrasonic waves, radio frequency waves, etc.) and the imaging detector 514 detects and receives the imaging beam. Alternatively, the imaging detector 514 may detect and receive a secondary imaging beam or an emission stimulated by the imaging beam from the imaging source (e.g., in an MRI or PET scan). In one embodiment, the diagnostic imaging system 510 may include two or more diagnostic imaging sources 512 and two or more corresponding imaging detectors 514. For example, two X-ray sources 512 may be disposed around a patient to be imaged, fixed at an angular separation from each other (e.g., 90 degrees, 45 degrees, etc.) and aimed through the patient toward corresponding imaging detectors 514, which may be diametrically opposed to the imaging sources 514. A single large imaging detector 514, or multiple imaging detectors 514, also may be illuminated by each X-ray imaging source 514. Alternatively, other numbers and configurations of imaging sources 512 and imaging detectors 514 may be used.

The imaging source 512 and the imaging detector 514 are coupled to the processing device 516, which controls the imaging operations and process image data within the diagnostic imaging system 510. In one embodiment, the processing device 516 may communicate with the imaging source 512 and the imaging detector 514. Embodiments of the processing device 516 may include one or more general-purpose processors (e.g., a microprocessor), special purpose processors such as a digital signal processor (DSP), or other type of devices such as a controller or field programmable gate array (FPGA). The processing device 516 also may include other components (not shown) such as memory, storage devices, network adapters, and the like. In one embodiment, the processing device 516 generates digital diagnostic images (also referred to herein as pretreatment images) in a standard format such as the Digital Imaging and Communications in Medicine (DICOM) format. In other embodiments, the processing device 516 may generate other standard or non-standard digital image formats.

Additionally, the processing device 516 may transmit diagnostic image files such as DICOM files to the treatment planning system 530 over a data link 560. In one embodiment, the data link 560 may be a direct link, a local area network (LAN) link, a wide area network (WAN) link such as the Internet, or another type of data link. Furthermore, the information transferred between the diagnostic imaging system 510 and the treatment planning system 530 may be either pulled or pushed across the data link 560, such as in a remote diagnosis or treatment planning configuration. For example, a user may utilize embodiments of the present invention to remotely diagnose or plan treatments despite the existence of a physical separation between the system user and the patient.

The illustrated treatment planning system 530 includes a processing device 532, a system memory device 534, an electronic data storage device 536, a display device 538, and an input device 540. The processing device 532, system memory 534, storage 536, display 538, and input device 540 may be coupled together by one or more communication channel 542 such as a bus.

The processing device 532 receives and processes image data. The processing device 532 also processes instructions and operations within the treatment planning system 530. In certain embodiments, the processing device 532 may include one or more general-purpose processors (e.g., a microprocessor), special purpose processors such as a digital signal processor (DSP), or other types of devices such as a controller or field programmable gate array (FPGA).

In particular, the processing device 532 may be configured to execute instructions for performing the operations discussed herein. For example, the processing device 532 may be configured to automatically control the timing of image acquisitions, automatically determine the specified times, and automatically trigger the imaging system to acquire images at the specified times. The processing device 532 may also be configured to execute instructions for performing other operations, such as, for example, the processing device 532 may identify a non-linear path of movement of a target within a patient and develop a non-linear model of the non-linear path of movement. In another embodiment, the processing device 532 may develop the non-linear model based on a multiple position points and multiple direction indicators. In another embodiment, the processing device 532 may generate multiple correlation models and select one of the models to derive a position of the target. Furthermore, the processing device 532 may facilitate other diagnosis, planning, and treatment operations related to the operations described herein.

In one embodiment, the processing device 532 is configured to perform the operations of the processing device 902, as described above, such as to automatically control the imaging system 905 to acquire images at specified times in the respiratory cycle to automatically generate a correlation model.

In one embodiment, the system memory 534 may include random access memory (RAM) or other dynamic storage devices. As described above, the system memory 534 may be coupled to the processing device 532 by the communication channel 542. In one embodiment, the system memory 534 stores information and instructions to be executed by the processing device 532. The system memory 534 also may be used for storing temporary variables or other intermediate information during execution of instructions by the processing device 532. In another embodiment, the system memory 534 also may include a read only memory (ROM) or other static storage device for storing static information and instructions for the processing device 532.

In one embodiment, the storage 536 is representative of one or more mass storage devices (e.g., a magnetic disk drive, tape drive, optical disk drive, etc.) to store information and instructions. The storage 536 and/or the system memory 534 also may be referred to as machine readable media. In a specific embodiment, the storage 536 may store instructions to perform the modeling operations discussed herein. For example, the storage 536 may store instructions to acquire and store data points, acquire and store images, identify non-linear paths, develop linear and/or non-linear correlation models, select a correlation model from multiple models, and so forth. In another embodiment, the storage 536 may include one or more databases. In one embodiment, the data stored in the storage device 903 of FIG. 9 is stored in either system memory 534 or storage 536.

In one embodiment, the display 538 may be a cathode ray tube (CRT) display, a liquid crystal display (LCD), or another type of display device. The display 538 displays information (e.g., a two-dimensional or three-dimensional representation of the VOI) to a user. The input device 540 may include one or more user interface devices such as a keyboard, mouse, trackball, or similar device. The input device(s) 540 may also be used to communicate directional information, to select commands for the processing device 532, to control cursor movements on the display 538, and so forth. In one embodiment, the display 538 and input device 540 are part of the user interface 901, described above with respect to FIG. 9.

Although one embodiment of the treatment planning system 530 is described herein, the described treatment planning system 530 is only representative of an exemplary treatment planning system 530. Other embodiments of the treatment planning system 530 may have many different configurations and architectures and may include fewer or more components. For example, other embodiments may include multiple buses, such as a peripheral bus or a dedicated cache bus. Furthermore, the treatment planning system 530 also may include Medical Image Review and Import Tool (MIRIT) to support DICOM import so that images can be fused and targets delineated on different systems and then imported into the treatment planning system 530 for planning and dose calculations. In another embodiment, the treatment planning system 530 also may include expanded image fusion capabilities that allow a user to plan treatments and view dose distributions on any one of various imaging modalities such as MRI, CT, PET, and so forth. Furthermore, the treatment planning system 530 may include one or more features of convention treatment planning systems.

In one embodiment, the treatment planning system 530 may share a database on the storage 536 with the treatment delivery system 550 so that the treatment delivery system 550 may access the database prior to or during treatment delivery. The treatment planning system 530 may be linked to treatment delivery system 550 via a data link 570, which may be a direct link, a LAN link, or a WAN link, as discussed above with respect to data link 560. Where LAN, WAN, or other distributed connections are implemented, any of components of the treatment system 500 may be in decentralized locations so that the individual systems 510, 530, 550 may be physically remote from one other. Alternatively, some or all of the functional features of the diagnostic imaging system 510, the treatment planning system 530, or the treatment delivery system 550 may be integrated with each other within the treatment system 500.

The illustrated treatment delivery system 550 includes a radiation source 552, an imaging system 905, a processing device 902, and a treatment couch 558. The radiation source 552, imaging system 905, processing device 902, and treatment couch 558 may be coupled to one another via one or more communication channel 560. One example of a treatment delivery system 550 is shown and described in more detail with reference to FIG. 17.

In one embodiment, the radiation source 552 is a therapeutic or surgical radiation source 552 to administer a prescribed radiation dose to a target in conformance with a treatment plan. For example, the target may be an internal organ, a tumor, a region. For convenience, reference herein to the target or a target refers to any whole or partial organ, tumor, region, or other delineated volume that is the subject of a treatment plan.

In one embodiment, the imaging system 905 of the treatment delivery system 550 captures intra-treatment images of a patient volume, including the target volume, for registration or correlation with the diagnostic images described above in order to position the patient with respect to the radiation source. Similar to the diagnostic imaging system 510, the imaging system 905 of the treatment delivery system 550 may include one or more sources and one or more detectors, and a processing device, as described above with respect to FIG. 9.

The treatment delivery system 550 also may include the processing device 902, as described in FIG. 9, to control the radiation source 552, the imaging system 905, and a treatment couch 558, which is representative of any patient support device. The processing device 902 may include one or more general-purpose processors (e.g., a microprocessor), special purpose processors such as a digital signal processor (DSP), or other devices such as a controller or field programmable gate array (FPGA). Additionally, the processing device 902 may include other components (not shown) such as memory, storage devices, network adapters, and the like.

Figure 17:
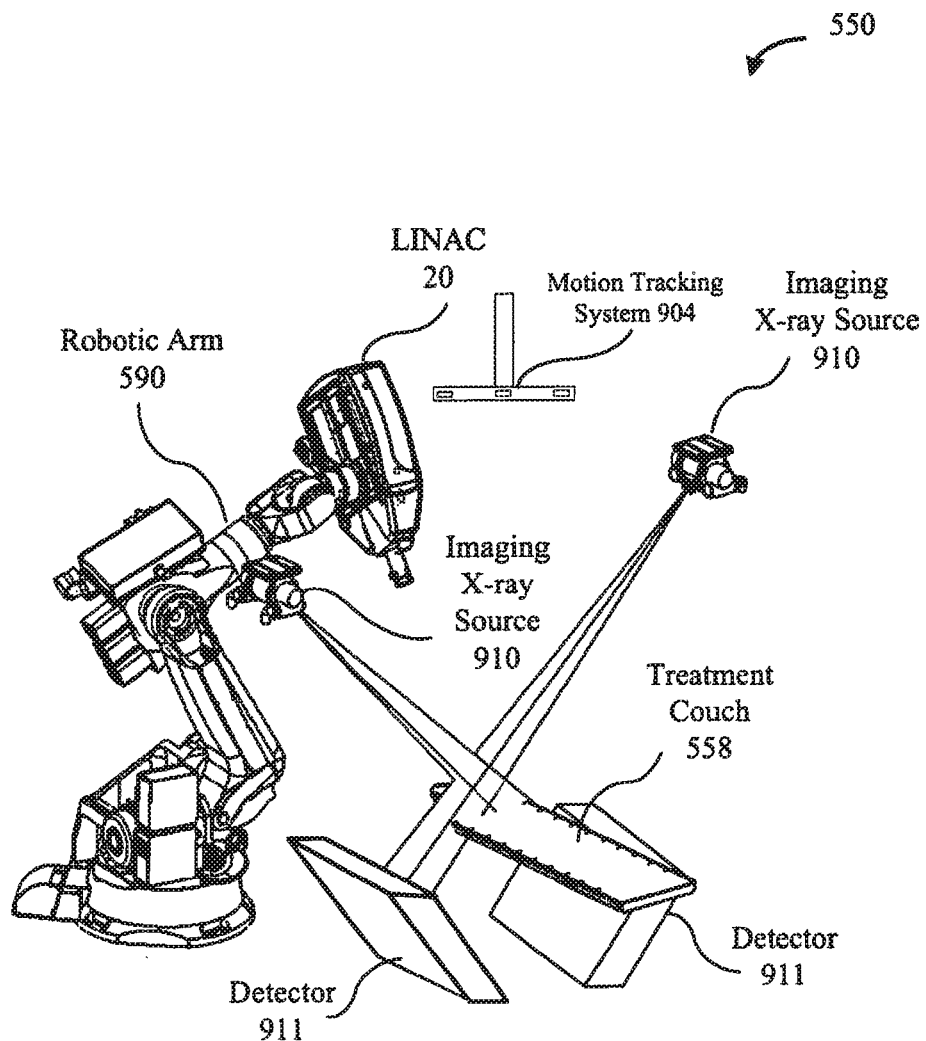
FIG. 17 is a schematic block diagram illustrating one embodiment of a treatment delivery system.

FIG. 17 is a schematic block diagram illustrating one embodiment of a treatment delivery system 550. The depicted treatment delivery system 550 includes a radiation source 552, in the form of a linear accelerator (LINAC) 20, and a treatment couch 558, as described above. The treatment delivery system 550 also includes multiple imaging X-ray sources 910 and detectors 911. The two X-ray sources 910 may be nominally aligned to project imaging X-ray beams through a patient from at least two different angular positions (e.g., separated by 90 degrees, 45 degrees, etc.) and aimed through the patient on the treatment couch 558 toward the corresponding detectors 911. In another embodiment, a single large imager may be used to be illuminated by each X-ray imaging source 910. Alternatively, other quantities and configurations of imaging sources 910 and detectors 911 may be used. The depicted treatment delivery system 550 also includes the motion tracking system 904 that tracks the motion of the external marker 25, as described above with respect to FIG. 9. In one embodiment, the treatment delivery system 550 may be an image-guided, robotic-based radiation treatment system (e.g., for performing radiosurgery) such as the CYBERKNIFE® system developed by Accuray Inc., Sunnyvale, Calif.

In the illustrated embodiment, the LINAC 20 is mounted on a robotic arm 590. The robotic arm 590 may have multiple (e.g., 5 or more) degrees of freedom in order to properly position the LINAC 20 to irradiate a target such as a pathological anatomy with a beam delivered from many angles in an operating volume around the patient. The treatment implemented with the treatment delivery system 550 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. In one embodiment, the treatment delivery system 550 delivers radiation beams according to the treatment plan without fixing the patient to a rigid, external frame to register the intra-operative position of the target volume with the position of the target volume during the pre-operative treatment planning phase.

As described above, the processing device 902 may implement algorithms to register images obtained from the imaging system 905 with pre-operative treatment planning images obtained from the diagnostic imaging system 510 in order to align the patient on the treatment couch 558 within the treatment delivery system 550. Additionally, these images may be used to precisely position the radiation source 552 with respect to the target volume or target.

In one embodiment, the treatment couch 558 may be coupled to second robotic arm (not shown) having multiple degrees of freedom. For example, the second arm may have five rotational degrees of freedom and one substantially vertical, linear degree of freedom. Alternatively, the second arm may have six rotational degrees of freedom and one substantially vertical, linear degree of freedom. In another embodiment, the second arm may have at least four rotational degrees of freedom. Additionally, the second arm may be vertically mounted to a column or wall, or horizontally mounted to pedestal, floor, or ceiling. Alternatively, the treatment couch 558 may be a component of another mechanism, such as the AXUM® treatment couch developed by Accuray Inc., Sunnyvale, Calif. In another embodiment, the treatment couch 558 may be another type of treatment table, including a conventional treatment table.

Although one exemplary treatment delivery system 550 is described above, the treatment delivery system 550 may be another type of treatment delivery system. For example, the treatment delivery system 550 may be a gantry based (isocentric) intensity modulated radiotherapy (IMRT) system, in which a radiation source 552 (e.g., a LINAC 20) is mounted on the gantry in such a way that it rotates in a plane corresponding to an axial slice of the patient. Radiation may be delivered from several positions on the circular plane of rotation. In another embodiment, the treatment delivery system 550 may be a stereotactic frame system such as the GAMMAKNIFE®, available from Elekta of Sweden.

Figure 18:
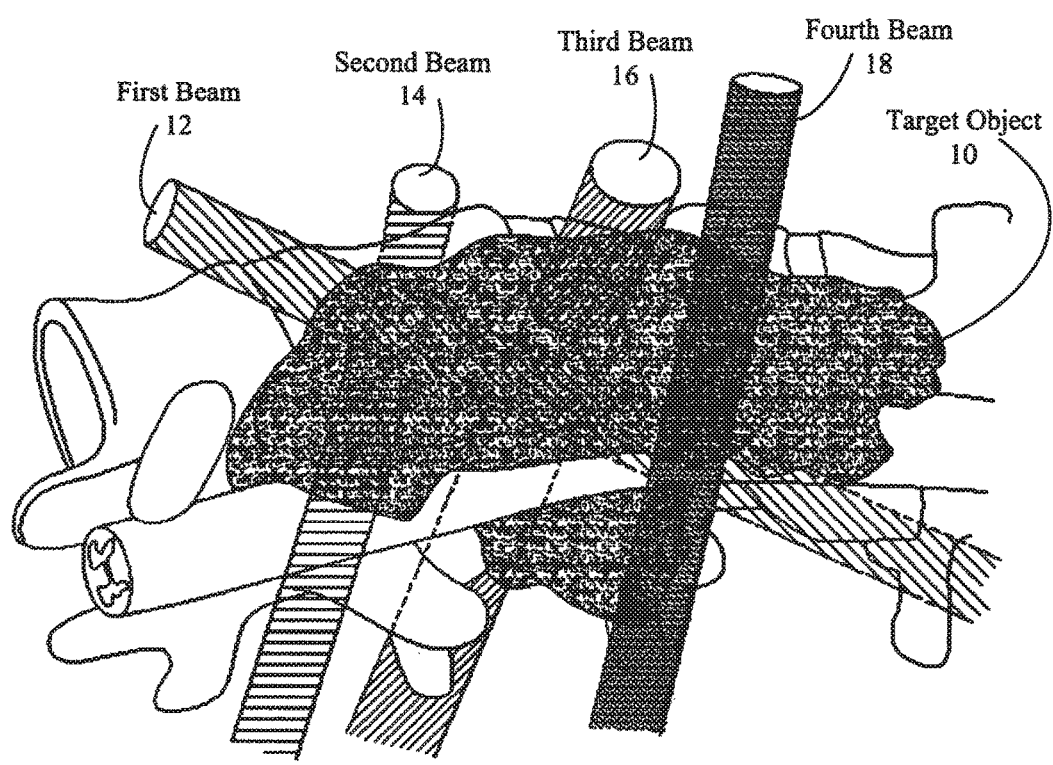
FIG. 18 illustrates a three-dimensional perspective view of a radiation treatment process.

FIG. 18 illustrates a three-dimensional perspective view of a radiation treatment process. In particular, FIG. 18 depicts several radiation beams directed at a target 10. In one embodiment, the target 10 may be representative of an internal organ, a region within a patient, a pathological anatomy such as a tumor or lesion, or another type of object or area of a patient. The target 10 also may be referred to herein as a target region, a target volume, and so forth, but each of these references is understood to refer generally to the target 10, unless indicated otherwise.

The illustrated radiation treatment process includes a first radiation beam 12, a second radiation beam 14, a third radiation beam 16, and a fourth radiation beam 18. Although four radiation beams 12-18 are shown, other embodiments may include fewer or more radiation beams. For convenience, reference to one radiation beam 12 is representative of all of the radiation beams 12-18, unless indicated otherwise. Additionally, the treatment sequence for application of the radiation beams 12-18 may be independent of their respective ordinal designations.

In one embodiment, the four radiation beams 12 are representative of beam delivery based on conformal planning, in which the radiation beams 12 pass through or terminate at various points within target 10. In conformal planning, some radiation beams 12 may or may not intersect or converge at a common point in three-dimensional space. In other words, the radiation beams 12 may be non-isocentric in that they do not necessarily converge on a single point, or isocenter. However, the radiation beams 12 may wholly or partially intersect at the target 10 with one or more other radiation beams 12.

In another embodiment, the intensity of each radiation beam 12 may be determined by a beam weight that may be set by an operator or by treatment planning software. The individual beam weights may depend, at least in part, on the total prescribed radiation dose to be delivered to target 10, as well as the cumulative radiation dose delivered by some or all of the radiation beams 12. For example, if a total prescribed dose of 3500 cGy is set for the target 10, the treatment planning software may automatically predetermine the beam weights for each radiation beam 12 in order to balance conformality and homogeneity to achieve that prescribed dose. Conformality is the degree to which the radiation dose matches (conforms to) the shape and extent of the target 10 (e.g., tumor) in order to avoid damage to critical adjacent structures. Homogeneity is the uniformity of the radiation dose over the volume of the target 10. The homogeneity may be characterized by a dose volume histogram (DVH), which ideally may be a rectangular function in which 100 percent of the prescribed dose would be over the volume of the target 10 and would be zero everywhere else.

The method described above offers many advantages, compared to currently know methods that are restricted to manually controlling the timing of image acquisitions. A first advantage, of course, is that this method automatically controls the timing of the image acquisitions to obtain model points that are substantially evenly distributed to develop a better correlation model than a correlation model developed using unsubstantially evenly-distributed model points. A second advantage is that this method can automatically determine the specified time in the respiratory cycle that corresponding to specified phases of the respiratory cycle.

In sum, a method and system are presented for automatically acquiring images of a target at specified times (corresponding to specified phases) of the respiratory cycle. The above described method and system can detect and identify whether a patient's internal organ moves (during respiration of the patient) along different paths during the inspiration and the expiration phases of the respiration, respectively. The above-described method allows a correlation model to be constructed, using the automatically acquired images, which can accurately estimate the position of an internal organ that either undergoes curvilinear movement, or moves along different paths during the inspiration and the expiration phases of the respiration, or both. Any other types of non-linear motion of an organ can also be fitted using curvilinear models as described above, by choosing appropriate parameter fitting models, e.g. higher-order polynomial fitting methods, as just one example. The method described above permits the targeting of internal lesions and/or tumors that move with respiration (or other patient motion), for purpose of delivering therapeutic radiation to the lesions and tumors.

While the method and system above have been described in conjunction with respiratory motion of the patient, other embodiments may track asymmetric, curvilinear (or otherwise nonlinear) motion of the internal organs that occur during any other type of motion of the patient, e.g. heartbeat. Also, although some of the embodiments described below are directed to controlling the timing of automatically acquiring images for model points in the breathing waveform (e.g., respiratory cycle), in other embodiments, the automatic image acquisition can be performed for other types of waveforms, such as heartbeat cycles of a patient, or other waveforms of other periodic motions of the patient. For example, instead of determining specific times or phases of the respiratory cycle, the method and system can determine specific times or phases of a cycle of a heart beat, or other periodic cycles of motion of the patient.

While the automatic correlation method and system have been particularly shown and described with reference to specific embodiments, it should be understood by those skilled in the art that various changes in form and detail may be made therein without departing from the spirit and scope of the invention.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by treatment planning software, such as the application of a beam (e.g., radiation, acoustic, etc.).

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   automatically triggering, by a processing device, image acquisition of a plurality of pretreatment images of a target, wherein the plurality of pretreatment images are internal to a patient, wherein acquisition of each of the plurality of pretreatment images is triggered at a different time; and
   generating, by the processing device, a correlation model distinguishing between inspiration and expiration movements that maps the movements of an external marker to a target location of the target using the plurality of pretreatment images, wherein said automatically triggering comprises automatically triggering image acquisition at substantially evenly-distributed points of a periodic cycle, and wherein said automatically triggering each of the plurality of pretreatment images comprises:
   obtaining historical data of movement of the target in one or more previous periodic cycles;
   dividing the historical data into a plurality of regions based on magnitude of movement of the target;
   distinguishing between the inspiration and expiration movements of the historical data;
   establishing a plurality of model metric regions using the plurality of regions and the distinguished inspiration and expiration movement, wherein the plurality of model metric regions correspond to a plurality of phases of the periodic cycle;
   determining whether a current sample of the target movement is in a desired phase of the periodic cycle by categorizing the current sample into one of the plurality of model metric regions; and
   sending an imaging command to an imaging system to acquire the pretreatment image when the current sample is in the desired phase of the periodic cycle.

2. The method of claim 1, wherein said obtaining comprises acquiring a plurality of data points representative of a corresponding plurality of positions over time of an external marker associated with a patient, wherein the plurality of positions of the external marker define an external path of movement of the external marker, and the external path of movement defines the periodic cycle of the patient.

3. The method of claim 2, wherein said generating the correlation model comprises:
   identifying a path of movement of the target based on the plurality of data points and the plurality of pretreatment images at the substantially evenly-distributed points of the periodic cycle; and
   developing the correlation model using the path of movement of the target.

4. The method of claim 2, further comprising updating the correlation model in response to an acquisition of a new data point.

5. The method of claim 1, further comprising:
deriving a target position of the target based on the correlation model,
sending a position signal associated with the target position to a beam generator controller; and
controlling the beam generator controller to direct a beam at the target.

6. The method of claim 1, further comprising:
periodically generating positional data about the target by automatically acquiring additional images of the target during treatment; and
continuously generating positional data about external motion of the external marker during treatment.

7. An apparatus, comprising:
a data storage device to store a plurality of pretreatment images of a target, wherein the plurality of pretreatment images are internal to a patient; and
a processing device coupled to the data storage device, the processing device to automatically trigger image acquisition of the plurality of pretreatment images, wherein acquisition of each of the plurality of pretreatment images is triggered at a different time, wherein the processing device is further to generate a correlation model distinguishing between inspiration and expiration movements that maps the movements of an external marker to a target location of the target using the plurality of pretreatment images, wherein in automatically triggering, the processing device is to automatically trigger image acquisition at substantially evenly-distributed points of a periodic cycle, and wherein in automatically triggering each of the plurality of pretreatment images, the processing device is further to:
obtain historical data of the movements of the target in one or more previous periodic cycles;
divide the historical data into a plurality of regions based on magnitude of movement of the target;
distinguish between the inspiration and expiration movements using the historical data;
establish a plurality of model metric regions using the plurality of regions and the distinguished inspiration and expiration movements, wherein the plurality of model metric regions correspond to a plurality of phases of the periodic cycle;
determine whether a current sample of the movements of the target is in a desired phase of the periodic cycle by categorizing the current sample into one of the plurality of model metric regions; and
send an imaging command to an imaging system to acquire the pretreatment image when the current sample is in the desired phase of the periodic cycle.

8. The apparatus of claim 7 wherein the processing device is to acquire a plurality of data points representative of a corresponding plurality of positions over time of the external marker associated with the patient, wherein the plurality of positions of the external marker define an external path of movement of the external marker, and the external path of movement defines the periodic cycle of the patient.

9. The apparatus of claim 8, wherein in generating the correlation model, the processing device is to:
identify a path of movement of the target based on the plurality of data points and the plurality of pretreatment images at the substantially evenly-distributed points of the periodic cycle; and
develop the correlation model using the path of movement of the target.

10. The apparatus of claim 1, wherein the processing device is further to:
derive a target position of the target based on the correlation model,
send a position signal associated with the target position to a beam generator controller; and
control the beam generator controller to direct a beam at the target.

11. The apparatus of claim 7, wherein the processing device is further to:
periodically generate positional data about the target by automatically acquiring additional images of the target during treatment; and
continuously generate positional data about external motion of the external marker during treatment of the patient.

* * * * *